United States Patent
Tsubota et al.

(10) Patent No.: US 8,212,219 B2
(45) Date of Patent: Jul. 3, 2012

(54) RADIATION DETECTING APPARATUS AND RADIATION IMAGE CAPTURING SYSTEM

(75) Inventors: Keiji Tsubota, Minami-ashigara (JP); Yasunori Ohta, Yokohama (JP); Naoyuki Nishino, Minami-ashigara (JP); Yutaka Yoshida, Fuchu (JP); Eiichi Kito, Minami-ashigara (JP); Shinji Imai, Hadano (JP); Yasuhiro Seto, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 364 days.

(21) Appl. No.: 12/585,431

(22) Filed: Sep. 15, 2009

(65) Prior Publication Data

US 2010/0078565 A1    Apr. 1, 2010

(30) Foreign Application Priority Data

Sep. 26, 2008    (JP) .................. 2008-247102

(51) Int. Cl.
    *G01T 1/24*    (2006.01)
(52) U.S. Cl. ................................. 250/370.08
(58) Field of Classification Search .......... 250/370.01, 250/370.08, 370.09, 370.14; 378/98.8
    See application file for complete search history.

(56) References Cited

U.S. PATENT DOCUMENTS

| | | | |
|---|---|---|---|
| 6,717,152 B2 | 4/2004 | Izumi | |
| 6,856,670 B2 | 2/2005 | Hoheisel | |
| 6,972,410 B2 | 12/2005 | Takeda et al. | |
| 7,183,556 B2 | 2/2007 | Yagi | |
| 7,488,946 B2 | 2/2009 | Hennessy et al. | |
| 7,705,317 B2 | 4/2010 | Miyaguchi | |
| 2003/0031296 A1* | 2/2003 | Hoheisel | 378/98.8 |
| 2007/0075253 A1 | 4/2007 | Misawa et al. | |

FOREIGN PATENT DOCUMENTS

| | | |
|---|---|---|
| JP | 01-064206 U | 4/1989 |
| JP | 10-282598 A | 10/1998 |
| JP | 2000-105297 | 4/2000 |
| JP | 2000-254115 A | 9/2000 |
| JP | 2001-095789 A | 4/2001 |
| JP | 2001-305224 A | 10/2001 |
| JP | 2002-090462 A | 3/2002 |
| JP | 2002-162474 A | 6/2002 |
| JP | 2002-311527 A | 10/2002 |
| JP | 2003-70776 | 3/2003 |
| JP | 2003-121553 A | 4/2003 |
| JP | 2003-172783 | 6/2003 |
| JP | 2004-361879 A | 12/2004 |
| JP | 2006-058168 A | 3/2006 |
| JP | 2006-263339 A | 10/2006 |
| JP | 2007-101256 A | 4/2007 |
| JP | 2008-090304 A | 4/2008 |
| JP | 2008-141705 A | 6/2008 |

* cited by examiner

*Primary Examiner* — Mark R Gaworecki
(74) *Attorney, Agent, or Firm* — Jean C. Edwards, Esq.; Edwards Neils PLLC

(57) ABSTRACT

A radiation detecting apparatus includes a radiation conversion panel for detecting radiation that has passed through a subject and converting the detected radiation into radiation image information, and a casing for storing the radiation conversion panel as a roll when the subject is not being irradiated with radiation. When the subject is irradiated with radiation, the radiation conversion panel stored as a roll in the casing is unrolled and pulled out of the casing, and the radiation conversion panel is extended flatwise against the subject.

15 Claims, 30 Drawing Sheets

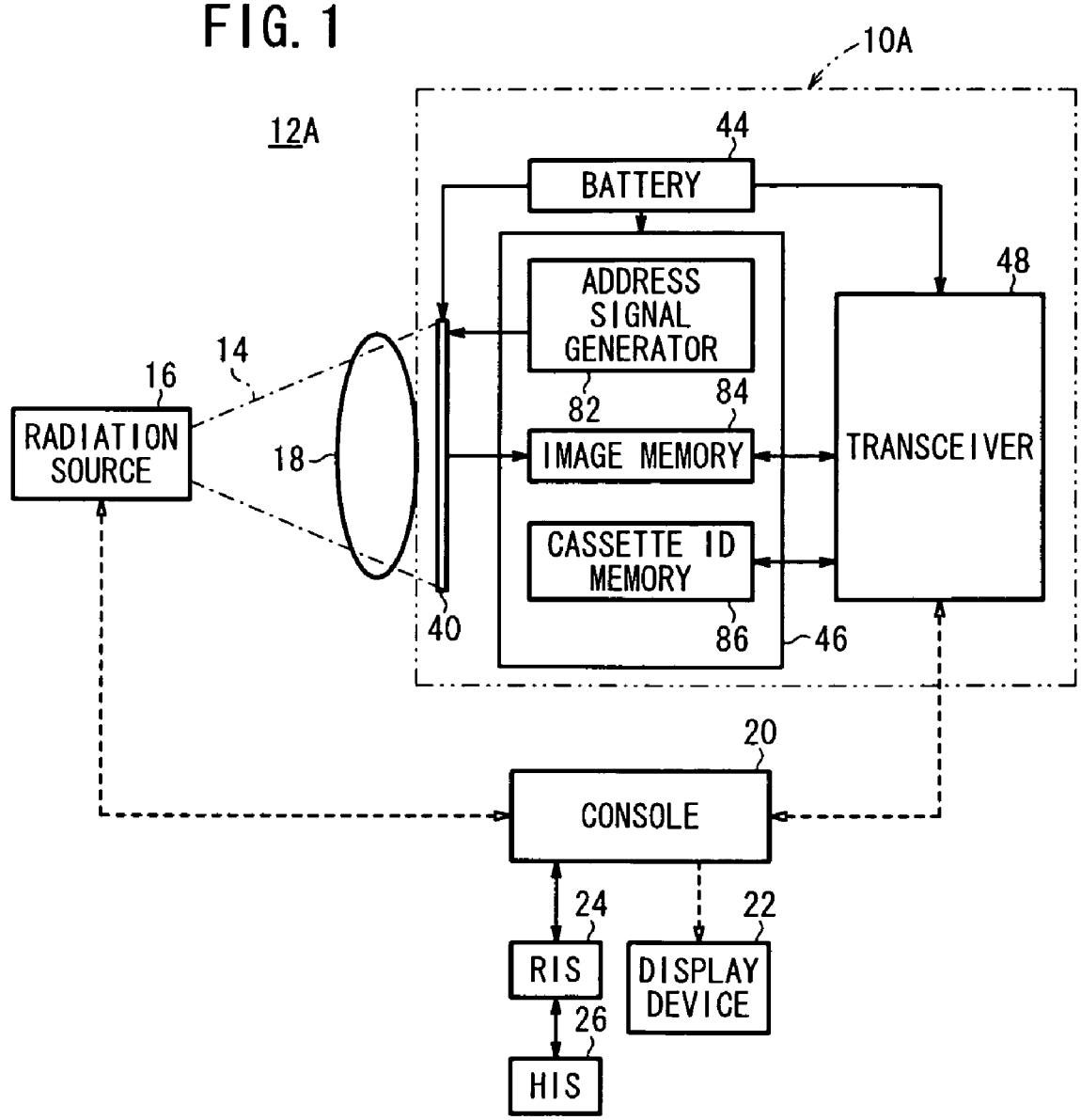

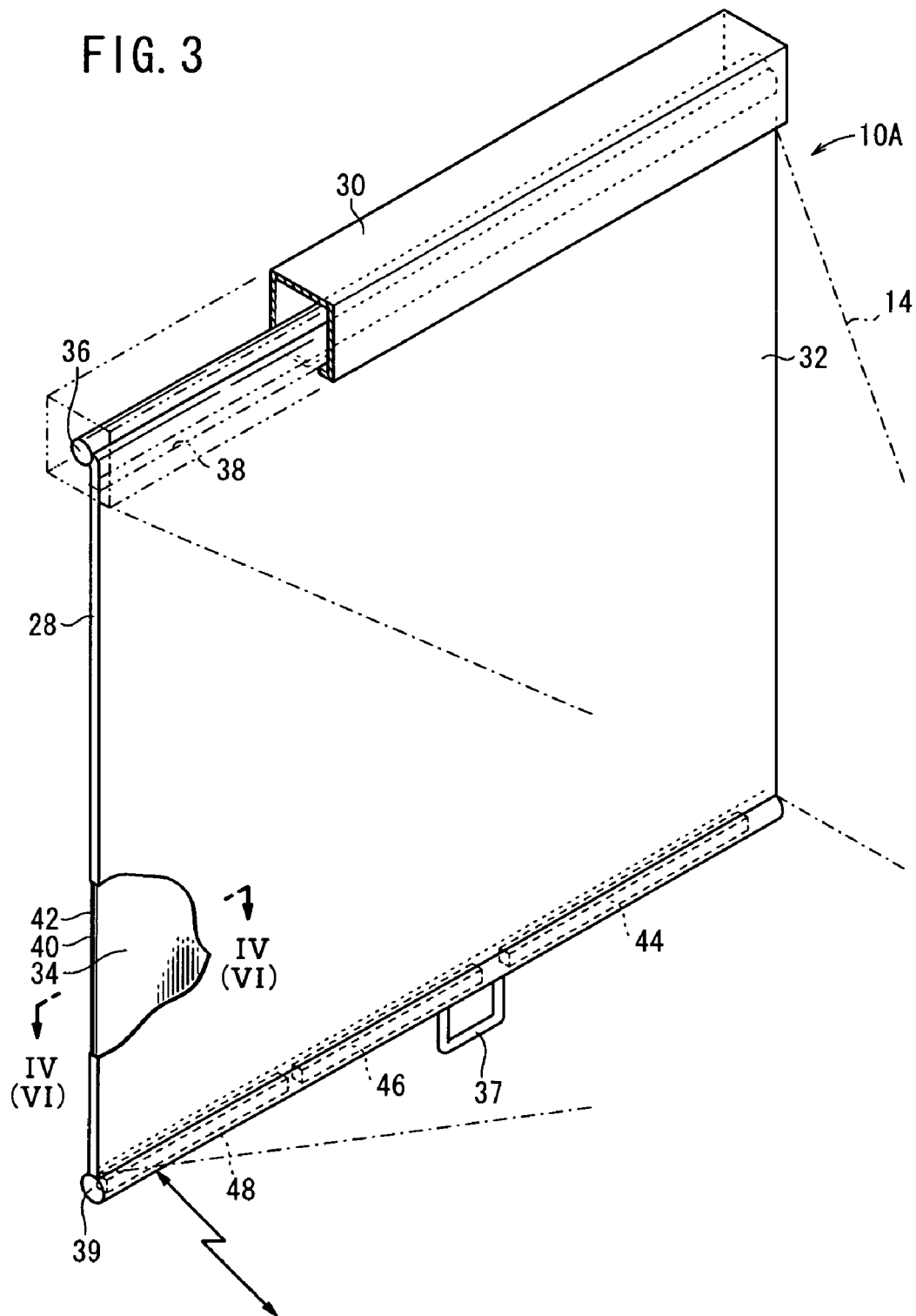

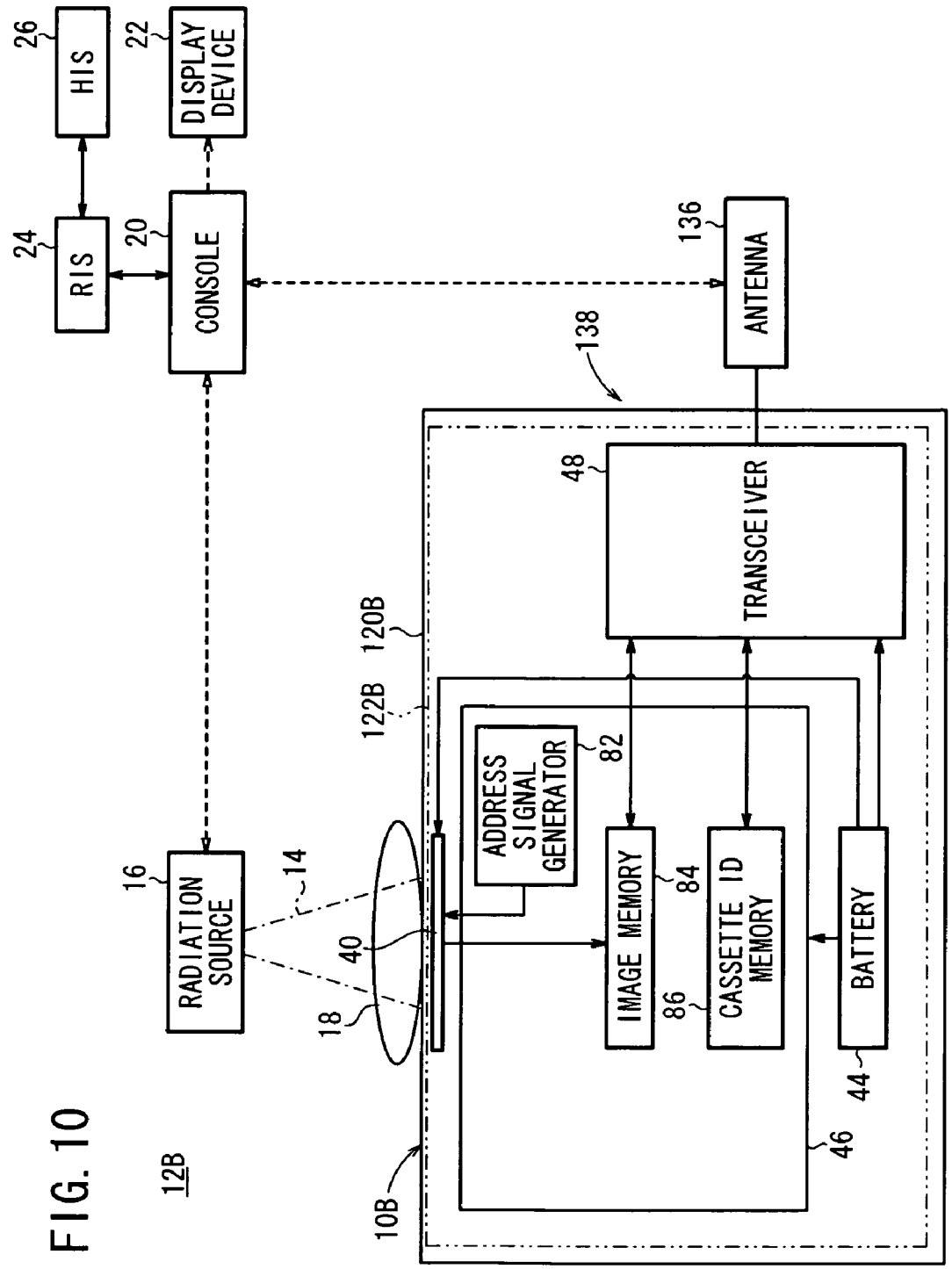

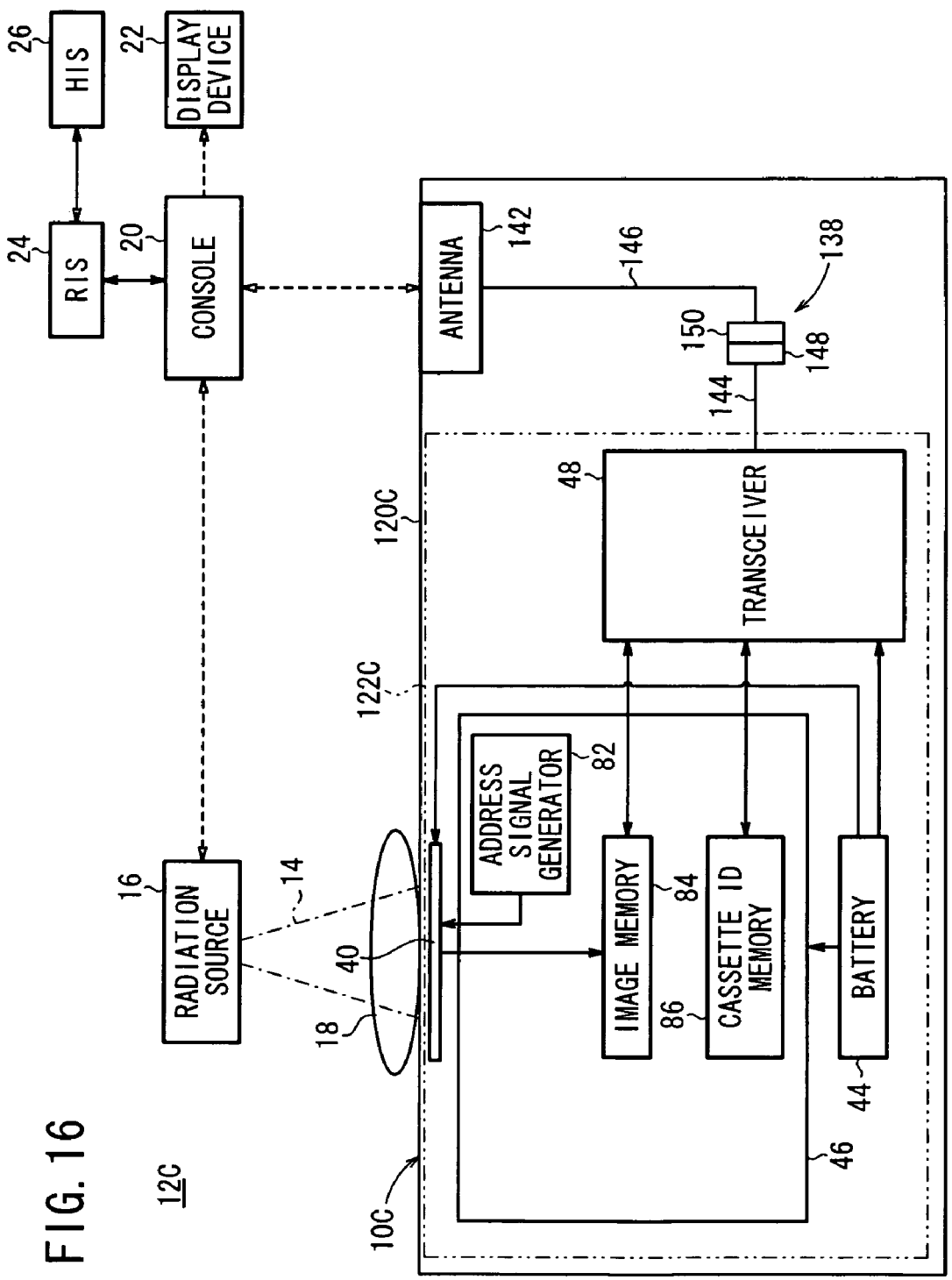

RADIATION DETECTING APPARATUS AND RADIATION IMAGE CAPTURING SYSTEM

CROSS-REFERENCE TO RELATED APPLICATION

This application is based upon and claims the benefit of priority from Patent Application No. 2008-247102 filed on Sep. 26, 2008, in the Japan Patent Office, of which the contents are incorporated herein by reference.

BACKGROUND OF THE INVENTION

1. Field of the Invention

The present invention relates to a radiation detecting apparatus for detecting radiation that has passed through a subject and converting the detected radiation into radiation image information, and a radiation image capturing system incorporating such a radiation detecting apparatus therein.

2. Description of the Related Art

In the medical field, there have widely been used radiation image capturing systems, which apply radiation to a subject and guide the radiation that has passed through the subject to a radiation conversion panel, which in turn captures a radiation image from such radiation. Known forms of radiation conversion panels include a conventional radiation film for recording a radiation image by way of exposure, and a stimulable phosphor panel for storing radiation energy representing a radiation image in a phosphor, and reproducing the radiation image as stimulated light by applying stimulating light to the phosphor.

The radiation film, with the radiation image recorded therein, is supplied to a developing device to develop the radiation image. Alternatively, the stimulable phosphor panel is supplied to a reading device in order to read the radiation image as a visible image.

In an operating room or the like, it is necessary to read recorded radiation image information immediately from a radiation conversion panel after the radiation image information has been captured therein for the purpose of quickly and appropriately treating the patient. As a radiation conversion panel which meets such a requirement, there has been developed a direct-conversion-type radiation detector including solid-state detectors for directly converting radiation into electric signals, or an indirect-conversion-type radiation detector comprising a scintillator for temporarily converting radiation into visible light, and solid-state detectors for converting the visible light into electric signals to read detected radiation image information.

Heretofore, there has been proposed a radiation detecting apparatus housing therein a radiation detector (radiation conversion panel), which is flexible enough to match itself to desired surface shapes of the patient, as disclosed in Japanese Laid-Open Patent Publication No. 2003-070776.

However, the flexible radiation detector or radiation conversion panel of the proposed radiation detecting apparatus cannot easily be placed in storage during periods when it is not used to detect radiation having passed through a subject, i.e., when it is not used to capture a radiation image of a subject. On the other hand, when the flexible radiation conversion panel is used to detect radiation having passed through a subject, i.e., when it is used to capture a radiation image of the subject, the irradiated surface (image-capturing surface) of the radiation conversion panel cannot be kept flat with respect to the subject.

Japanese Laid-Open Patent Publication No. 2003-070776 discloses a flexible radiation detector or radiation conversion panel, which includes a scintillator for converting radiation that has passed through a subject into visible light, and solid-state detectors for converting the visible light into electric signals representative of radiation image information. Such a flexible radiation detector or radiation conversion panel is housed in a flexible case.

When external light is applied to the radiation conversion panel, the solid-state detectors convert the visible light converted from the radiation by the scintillator and also external light into electric signals. Therefore, a signal component of the electric signals, which corresponds to the external light, results in noise with respect to the radiation image information. Although it is desirable that the radiation conversion panel be shielded against external light to eliminate such noise, there is nothing disclosed in Japanese Laid-Open Patent Publication No. 2003-070776 for shielding the radiation conversion panel against external light.

Japanese Laid-Open Patent Publication No. 2003-172783 discloses a cassette-type radiation detecting apparatus incorporating solid-state detectors. The disclosed cassette-type radiation detecting apparatus is rigid as a whole, and therefore cannot be matched to the surface shape of a patient to be imaged. Further, the cassette-type radiation detecting apparatus is so heavy that it cannot be handled with ease.

As described above, Japanese Laid-Open Patent Publication No. 2003-070776 discloses a flexible radiation detecting apparatus, which can match itself to the surface shape of a patient to be imaged thereby. However, since the disclosed radiation detecting apparatus includes drive circuits, which are disposed in a direction in which the radiation detecting apparatus itself is flexible, the radiation detecting apparatus is not sufficiently flexible. Furthermore, the disclosed radiation detecting apparatus includes readout amplifiers, which tend to limit the flexibility thereof.

SUMMARY OF THE INVENTION

A first object of the present invention is to enable a flexible radiation conversion panel to be kept in storage with ease when it is not being used to capture a radiation image of a subject. Further, the radiation conversion panel is capable of keeping its image-capturing surface flat with respect to a subject when it is used to capture a radiation image of the subject.

A second object of the present invention is to shield a radiation conversion panel reliably against external light, for thereby acquiring highly accurate radiation image information.

A third object of the present invention is to provide a radiation detecting apparatus which is sufficiently flexible, flat, and lightweight.

To achieve the first object, in accordance with the present invention, a radiation detecting apparatus is provided, comprising a radiation conversion panel for detecting radiation that has passed through a subject and converting the detected radiation into radiation image information, and a casing for storing the radiation conversion panel therein as a roll when the subject is not irradiated with the radiation, wherein when the subject is irradiated with the radiation, the radiation conversion panel stored as the roll in the casing is unrolled and pulled out of the casing, and extended flatwise against the subject.

According to the present invention, the flexible radiation conversion panel is rolled and stored in the casing when it is not being used to capture a radiation image of the subject. The flexible radiation conversion panel is pulled out of the casing and extended flatwise against the subject when it is used to capture a radiation image of the subject. Therefore, when the radiation conversion panel is not being used to capture a radiation image of the subject, the radiation conversion panel can easily be stored. Also, when the radiation conversion panel is used to capture a radiation image of the subject, the image capturing surface thereof can easily be extended flatwise against the subject.

To achieve the second object, in accordance with the present invention, a radiation detecting apparatus is provided, comprising a radiation conversion panel which includes a scintillator for converting radiation that has passed through a subject into visible light and a plurality of solid-state detectors for converting the visible light into electric signals, and a storage body for storing the radiation conversion panel therein, wherein the storage body blocks external light and is permeable to the radiation.

According to the present invention, since the storage body for storing the radiation conversion panel therein blocks external light and is permeable to radiation, the storage body reliably shields the radiation conversion panel from external light, while allowing the radiation detecting apparatus to acquire highly accurate radiation image information.

To achieve the third object, in accordance with the present invention, a radiation detecting apparatus is provided, which is disposed on a flexible substrate, comprising a matrix of switching devices having signal electrodes connected to signal lines, gate electrodes connected to gate lines, and other signal electrodes connected to pixels for detecting radiation that has passed through a subject and converting the detected radiation into signal charges, the pixels being disposed respectively on the switching devices, a bias capacitor for applying a bias voltage to the pixels, and input terminals of the gate lines, output terminals of the signal lines, and a bias input terminal for supplying the bias voltage to the bias capacitor.

According to the present invention, since the matrix of switching devices with the pixels disposed thereon, the bias capacitor for applying a bias voltage to the pixels, and the input and output terminals are disposed on the flexible substrate, the radiation detecting apparatus is flexible, flat, and lightweight.

To achieve the third object, in accordance with the present invention, a radiation detecting apparatus is provided, which is disposed on a flexible substrate, comprising a matrix of switching devices having signal electrodes connected to signal lines, gate electrodes connected to gate lines, and other signal electrodes connected to pixels for detecting radiation that has passed through a subject and converting the detected radiation into signal charges, the pixels being disposed respectively on the switching devices, a bias capacitor for applying a bias voltage to the pixels, a gate IC connected to the gate lines for energizing columns or rows of the switching devices through the gate lines, and drive terminals of the gate IC, output terminals of the signal lines, and a bias input terminal for supplying the bias voltage to the bias capacitor.

According to the present invention, since the included gate IC is spaced from the switching devices by a short physical distance, the switching devices are energized at a high speed, and as a result, the signal charges stored in the pixels can be read at a high speed.

To achieve the third object, in accordance with the present invention, a radiation detecting apparatus is provided comprising a radiation detecting circuit unit disposed on a flexible substrate, and a control circuit unit for controlling the radiation detecting circuit unit, wherein the radiation detecting circuit unit comprises a matrix of switching devices having signal electrodes connected to signal lines, gate electrodes connected to gate lines, and other signal electrodes connected to pixels for detecting radiation that has passed through a subject and converting the detected radiation into signal charges, the pixels being disposed respectively on the switching devices, a bias capacitor for applying a bias voltage to the pixels, and input terminals of the gate lines, output terminals of the signal lines, and a bias input terminal for supplying the bias voltage to the bias capacitor, and wherein the control circuit unit comprises a drive circuit for energizing columns of the switching devices, and a signal reading circuit for reading signal charges from rows of the pixels through energized columns of the switching devices.

According to the present invention, inasmuch as the radiation detecting circuit unit, which comprises the matrix of switching devices with the pixels disposed thereon, the bias capacitor for applying a bias voltage to the pixels, and the input and output terminals, is disposed on the flexible substrate, the radiation detecting circuit unit is made flexible. Since the radiation detecting circuit unit does not include the control circuit unit therein, the radiation detecting circuit unit is flat and lightweight. Since the radiation detecting circuit unit can be flexed into conformity with the surface configuration of the patient, the radiation detecting circuit unit is less burdensome on the patient.

To achieve the third object, in accordance with the present invention, a radiation detecting apparatus is provided comprising a radiation detecting circuit unit disposed on a flexible substrate, and a control circuit unit for controlling the radiation detecting circuit unit, wherein the radiation detecting circuit unit comprises a matrix of switching devices having signal electrodes connected to signal lines, gate electrodes connected to gate lines, and other signal electrodes connected to pixels for detecting radiation that has passed through a subject and converting the detected radiation into signal charges, the pixels being disposed respectively on the switching devices, a gate IC for energizing columns of the switching devices, a bias capacitor for applying a bias voltage to the pixels, and input terminals of the gate lines, output terminals of the signal lines, and a bias input terminal for supplying the bias voltage to the bias capacitor, and wherein the control circuit unit comprises a gate IC drive circuit for energizing the gate IC, and a signal reading circuit for reading signal charges from rows of the pixels through energized columns of the switching devices.

According to the present invention, since the gate IC included in the radiation detecting circuit unit is spaced from the switching devices by a short physical distance, the switching devices are energized at a high speed, and as a result, the signal charges stored in the pixels can be read at a high speed.

In the above radiation detecting apparatus, a battery for supplying electric power to the control circuit unit may be mounted in the control circuit unit, or the battery may be separate from the control circuit unit.

If the battery is separate from the control circuit unit and replaceable, then a plurality of replaceable batteries may be provided, and numerous amounts of radiation image information of the subject or a plurality of subjects may be obtained using replaceable batteries.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 1 is a block diagram of a radiation detecting apparatus and a radiation image capturing system according to a first embodiment of the present invention;

FIG. 3 is a perspective view, partially cut away, of the radiation detecting apparatus shown in FIG. 1;

FIG. 10 is a block diagram of a radiation detecting apparatus and a radiation image capturing system according to a second embodiment of the present invention;

FIG. 16 is a block diagram of a radiation detecting apparatus and a radiation image capturing system according to a third embodiment of the present invention;

DESCRIPTION OF THE PREFERRED EMBODIMENTS

Figure 2B:
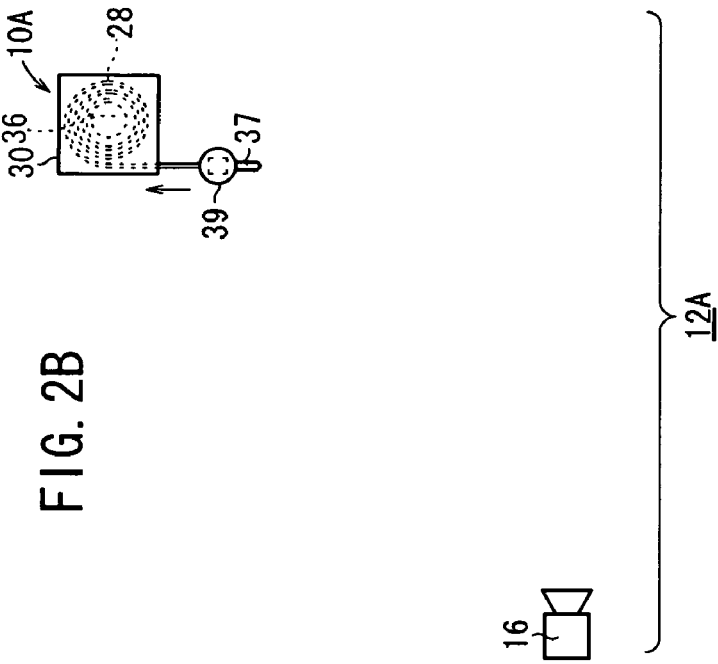
FIG. 2B is a side elevational view of the radiation detecting apparatus when a radiation image of a subject is not being captured.

Like or corresponding parts are denoted by like or corresponding reference characters throughout the views.

First, a radiation detecting apparatus (hereinafter also referred to as a "radiation detecting cassette") 10A according to a first embodiment of the present invention, and a radiation image capturing system 12A incorporating the radiation detecting apparatus 10A therein, will be described below with reference to FIGS. 1 through 9.

As shown in FIG. 1, the radiation image capturing system 12A according to the first embodiment of the present invention includes a radiation source 16 for irradiating a patient 18 as a subject with radiation 14 at a dose depending on image capturing conditions, a radiation detecting cassette 10A having a radiation detector or radiation conversion panel 40 for detecting radiation 14 that has passed through the patient 18, a display device 22 for displaying radiation image information based on the radiation 14 which has been detected by the radiation detector 40, and a console (controller) 20 for controlling the radiation detecting cassette 10A, the radiation source 16, and the display device 22.

Signals are sent and received between the console 20, the radiation detecting cassette 10A, the radiation source 16, and the display device 22, based on wireless LAN (Local Area Network) communications or wireless millimeter-wave communications such as UWB (Ultra-WideBand) technology, IEEE 802.11.a/g/n, or the like.

The console 20 is connected to a radiology information system (RIS) 24, which generally manages radiation image information handled by the radiological department of the hospital, together with other information. The RIS 24 is connected to a hospital information system (HIS) 26, which generally manages medical information within the hospital.

Figure 2A:
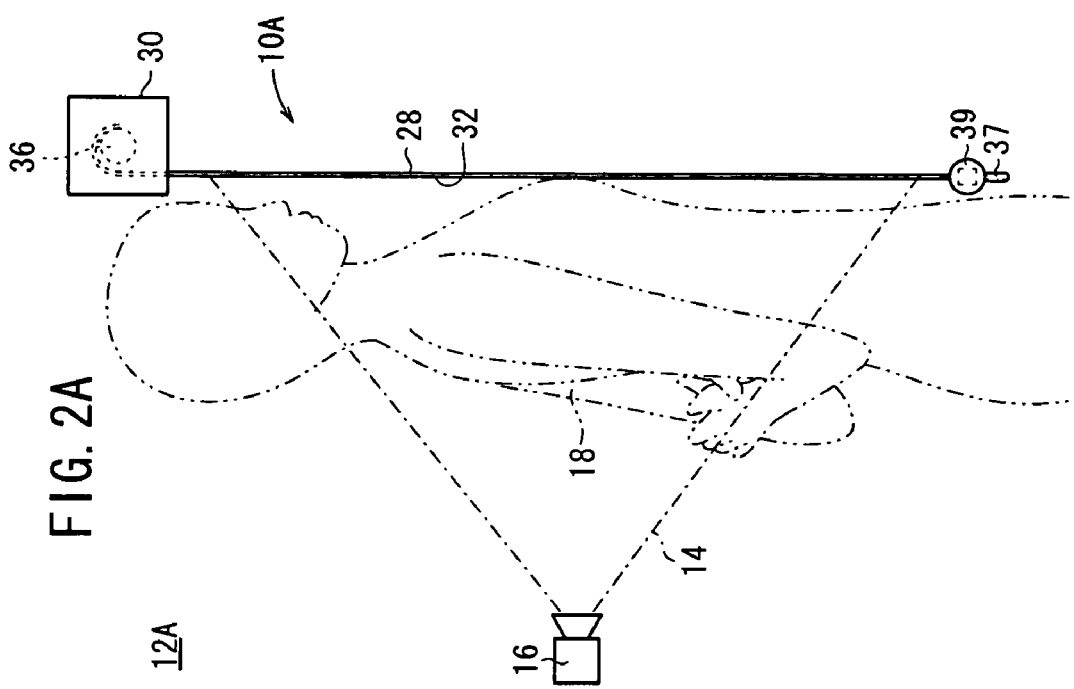
FIG. 2A is a side elevational view of the radiation detecting apparatus when a radiation image of a subject is captured.

As shown in FIGS. 2A through 3, the radiation detecting cassette 10A is in the shape of a roll screen in appearance, and includes a flexible screen 28 made of a material that is permeable to radiation 14, and further having a proximal end coupled to a takeup shaft 36 disposed in a storage box (casing) 30, and a distal end coupled to a weight bar 39. When the screen 28 is not used to detect radiation 14 having passed through the patient 18, i.e., when the screen 28 is not used to capture a radiation image of the patient 18, the screen 28 is wound into a roll and stored in the storage box 30 (see FIG. 2B). When the screen 28 is used to detect radiation 14 having passed through the patient 18, i.e., when the screen 28 is used to capture a radiation image of the patient 18, the doctor or a radiological technician pulls down a handle 37 connected to the weight bar 39, thereby pulling the screen 28 out of the storage box 30 through a slot 38 defined in the bottom of the storage box 30, until the screen 28 is extended vertically and is arranged substantially flatwise against the patient 18 (see FIGS. 2A and 3).

The screen 28 is made of a flexible resin such as polyethylene (PE), polyethylene terephthalate (PET), polyvinyl chloride (PVC), polyvinylidene chloride (PVDC), polylactic acid (PLA), polypropylene (PP), polyamide (PA), polycarbonate (PC), polytetrafluoroethylene (PTFE), polyurethane (PU), polystyrene (PS), polyester, an ABS resin, acrylic resin (PMMA), polyacetal (POM), or the like, or from a sheet metal such as aluminum, aluminum oxide, stainless steel, or the like.

The radiation detecting cassette 10A may be of a suspended structure secured to the ceiling by support members, not shown, or an upstanding structure, which is placed on a floor by a tripod, not shown. According to the first embodiment, therefore, as shown in FIG. 2A, the radiation detecting cassette 10A captures a radiation image of the patient 18 while radiation 14 is applied from the radiation source 16 toward the patient 18 standing in an upright posture (an upright image capturing process).

The screen 28 houses therein a grid 34 for removing scattered rays of radiation 14 from the patient 18, a radiation detector 40 for detecting radiation 14 that has passed through the patient 18, and a lead sheet 42 for absorbing back scattered rays from the radiation 14, which are successively arranged in this order from an irradiated surface (image-capturing surface) 32 facing the patient 18. The irradiated surface 32 of the screen 28 may be constructed as the grid 34.

Figure 4:
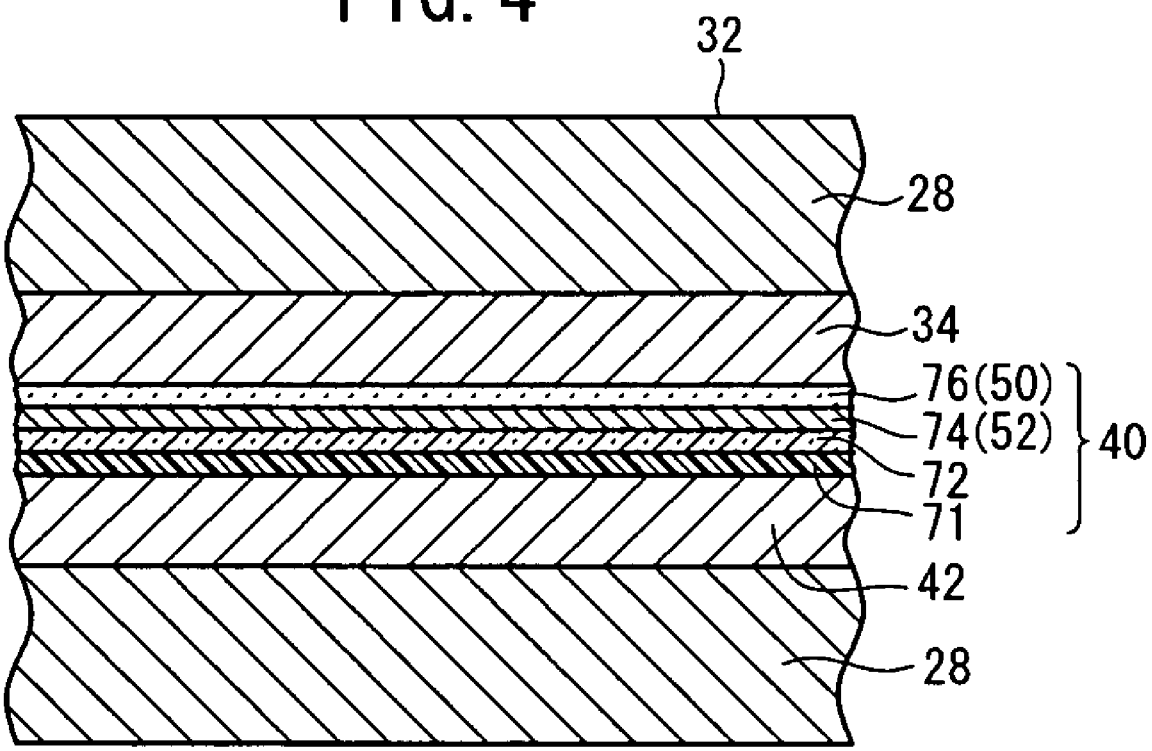
FIG. 4 is a cross-sectional view taken along line IV-IV of FIG. 3.

As shown in FIG. 4, the radiation detector 40 comprises a substrate 71, a scintillator 72 disposed on the substrate 71 made of a phosphor, such as GOS ($Gd_2O_2S$) or CsI:Tl, as a matrix for converting radiation 14 that has passed through the patient 18 into visible light, a TFT layer 74 disposed on the scintillator 72 and including a matrix of thin-film transistors (TFTs) 52 (see FIG. 5), the TFT layer 74 being permeable to radiation 14 and visible light, and a photoelectric transducer layer 76 disposed on the TFT layer 74 and including solid-state detectors (hereinafter referred to as "pixels") 50 made of a material such as amorphous silicon (a-Si) or the like, for converting the visible light into electric signals.

The substrate 71 may be made of polyethylene terephthalate (PET), polyethylene naphthalate (PEN), polyimide (e.g., Kapton (registered trademark) of DuPont), polysulfone ether (PES), polycarbonate (PC), or the like, as disclosed in Japanese Laid-Open Patent Publication No. 2003-070776.

As shown in FIG. 3, the weight bar 39 houses therein a battery 44 serving as a power supply for the radiation detecting cassette 10A, a cassette controller 46 for energizing the radiation detector 40 with electric power supplied from the battery 44, and a transceiver (wireless communicating unit) 48 for sending and receiving signals including radiation information detected by the radiation detector 40 to and from the console 20. Lead plates or the like preferably should be placed on the side of the weight bar 39 near the irradiated surface 32, over the cassette controller 46 and the transceiver 48, for protection against damage, which would be caused if radiation 14 were applied to the cassette controller 46 and the transceiver 48. The battery 44 supplies electric power to the radiation detector 40, the cassette controller 46, and the transceiver 48 in the radiation detecting cassette 10A.

Figure 5:
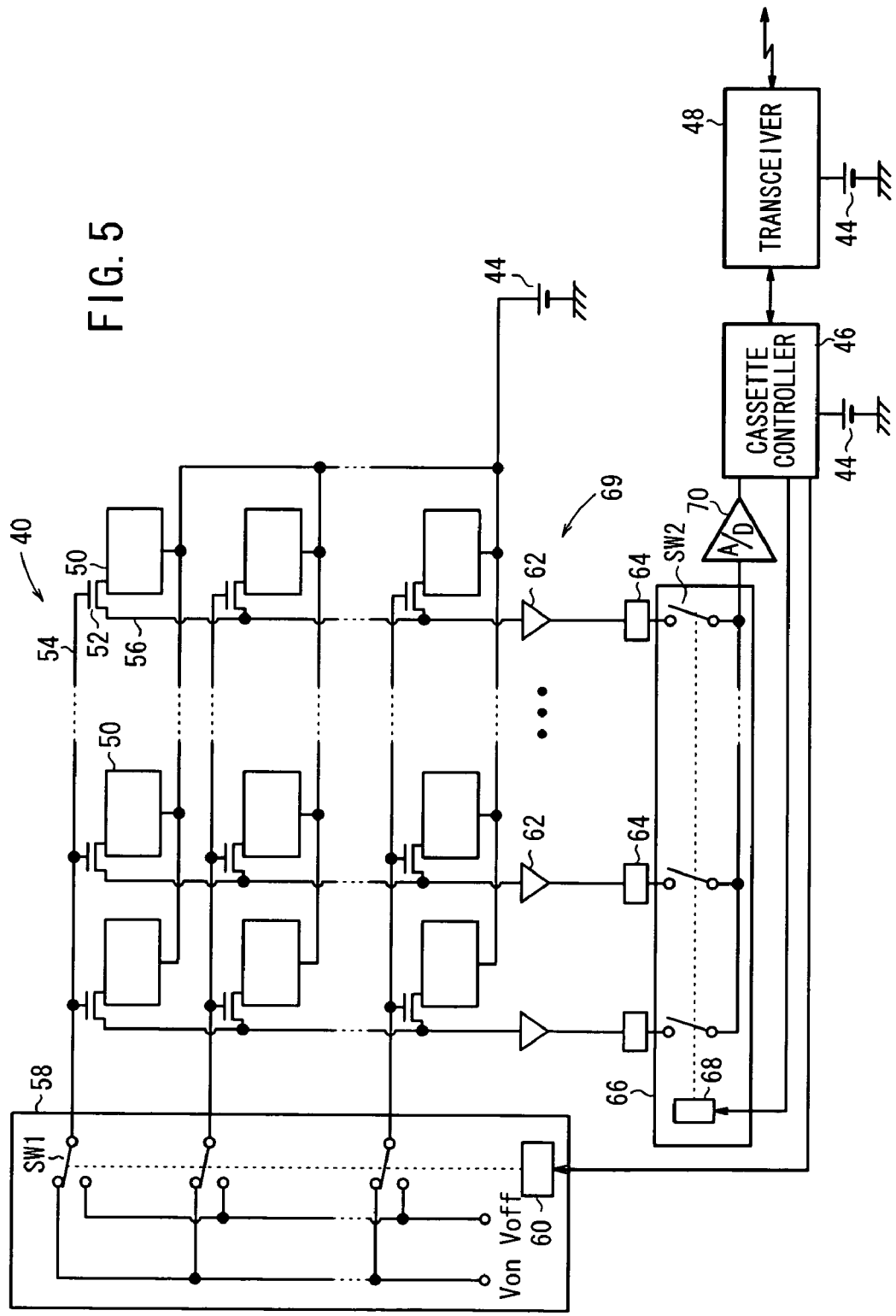
FIG. 5 is a block diagram of a circuit arrangement of the radiation detecting apparatus shown in FIG. 1.

As shown in FIG. 5, the radiation detector 40 comprises an array of thin-film transistors (TFTs) 52 arranged in rows and columns (the TFT layer 74), with the photoelectric transducer layer 76 (see FIG. 4) being disposed on the array of TFTs 52. When radiation 14 is applied to the radiation detector 40, the photoelectric transducer layer 76 generates electric charges, and the pixels 50 store the generated electric charges. Then, the TFTs 52 are turned on each row at a time to read the electric charges from the pixels 50 as an image signal.

The TFTs 52 connected to the respective pixels 50 are connected to respective gate lines 54 extending parallel to the rows, and respective signal lines 56 extending parallel to the columns. The gate lines 54 are connected to a line scanning driver 58, and the signal lines 56 are connected to a multiplexer 66. The gate lines 54 are supplied with control signals Von, Voff for turning on and off the TFTs 52 along the rows from the line scanning driver 58. The line scanning driver 58 comprises a plurality of switches SW1 for switching between the gate lines 54, and an address decoder 60 for outputting a selection signal for selecting one of the switches SW1 at a time. The address decoder 60 is supplied with an address signal from the cassette controller 46.

The signal lines 56 are supplied with electric charges stored in the pixels 50 through the TFTs 52 arranged in the columns. Electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56, and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal, which is generated by the multiplexer 66 based on electric charges from the sample and hold circuits 64, is converted by the A/D converter 70 into a digital image signal representing radiation image information, which is supplied to the cassette controller 46. The amplifiers 62, the sample and hold circuits 64, the multiplexer 66, and the A/D converter 70 serve as a reading circuit (reader) 69 for reading electric charges (electric signals) from the pixels 50, and acquiring the read electric charges as radiation image information.

The TFTs 52, which function as switching devices, may be combined with another image capturing device, such as a CMOS (Complementary Metal-Oxide Semiconductor) image sensor or the like. Alternatively, the TFTs 52 may be replaced with a CCD (Charge-Coupled Device) image sensor for shifting and transferring electric charges with shift pulses corresponding to gate signals in the TFTs.

As shown in FIG. 1, the cassette controller 46 of the radiation detecting cassette 10A includes an address signal generator 82, an image memory 84, and a cassette ID memory 86.

The address signal generator 82 supplies address signals to the address decoder 60 of the line scanning driver 58, and to the address decoder 68 of the multiplexer 66 of the radiation detector 40. The image memory 84 stores the radiation image information detected by the radiation detector 40. The cassette ID memory 86 stores cassette ID information for identifying the radiation detecting cassette 10A.

The transceiver 48 transmits the cassette ID information stored in the cassette ID memory 86 and the radiation image information stored in the image memory 84 to the console 20 by way of wireless communications.

The radiation detecting cassette 10A and the radiation image capturing system 12A according to the first embodiment are basically constructed as described above. Operations of the radiation detecting cassette 10A and the radiation image capturing system 12A will be described below.

Patient information of the patient 18 to be imaged is registered in the console 20 in advance, prior to commencing an image capturing process. If a region to be imaged and an image capturing method are known beforehand, then such image capturing conditions also are registered in the console 20.

For capturing radiation image information of the patient 18, the doctor or a radiological technician pulls the handle 37 downward to draw the screen 28 out of the storage box 30. As the screen 28 is drawn downward, the irradiated surface 32 of the screen 28 is extended vertically and substantially flat, under the total weight of the weight bar 39, the battery 44, the cassette controller 46, and the transceiver 48, which are housed in the weight bar 39. Then, the doctor or the radiological technician brings the patient 18 into an upright position facing the irradiated surface 32 of the flat screen 28. After having moved the radiation source 16 to a position facing the irradiated surface 32 of the flat screen 28, the doctor or the radiological technician operates an image capturing switch, not shown, of the radiation source 16 in order to initiate an upright image capturing process on the patient 18.

When the image capturing switch is operated, the radiation source 16 sends a request to the console 20 to transmit the image capturing conditions by way of wireless communications. In response to this request, the console 20 transmits the image capturing conditions to the radiation source 16 with respect to the region to be imaged of the patient 18. When the radiation source 16 receives the image capturing conditions, the radiation source 16 applies radiation 14 to the patient 18 at a dose according to the image capturing conditions.

Radiation 14 that has passed through the patient 18 is applied to the grid 34 of the radiation detecting cassette 10A, which removes scattered rays from the radiation 14. Then, the radiation 14 is applied to the radiation detector 40. The scintillator 72 of the radiation detector 40 emits visible light, at an intensity that depends on the intensity of the applied radiation 14. The pixels 50 of the photoelectric transducer layer 76 convert the visible light into electric signals and store the signals as electric charges. The stored electric charges, which represent radiation image information of the patient 18, are read from the pixels 50 according to address signals, which are supplied from the address signal generator 82 of the cassette controller 46 to the line scanning driver 58 and the multiplexer 66.

More specifically, in response to the address signals supplied from the address signal generator 82, the address decoder 60 of the line scanning driver 58 outputs a selection signal to select one of the switches SW1, which supplies the control signal Von to the gates of the TFTs 52, which are connected to the gate line 54 corresponding to the selected switch SW1. In response to the address signals supplied from the address signal generator 82, the address decoder 68 of the multiplexer 66 outputs a selection signal, so as to successively turn on the switches SW2 to switch between the signal lines 56, for thereby reading the electric charges stored in the pixels 50 connected to the selected gate line 54 through the signal lines 56.

The electric charges read from the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into digital signals. Digital signals, which represent the radiation image information, are stored in the image memory 84 of the cassette controller 46.

Similarly, the address decoder 60 of the line scanning driver 58 successively turns on the switches SW1 to switch between the gate lines 54 according to the address signal supplied from the address signal generator 82. The electric charges stored in the pixels 50 connected to the successively selected gate lines 54 are read through the signal lines 56, and processed by the multiplexer 66 and the A/D converter 70 into digital signals, which are stored in the image memory 84 of the cassette controller 46.

The radiation image information stored in the image memory 84 is transmitted from the transceiver 48 to the console 20 by way of wireless communications. The console 20 performs predetermined image processing on the received radiation image information, and stores the processed radiation image information in a memory, in association with the registered patient information of the patient 18. The processed radiation image information is transmitted from the console 20 to the display device 22, which displays a radiation image based on the radiation image information.

After the upright image capturing process on the patient 18 has been completed, the doctor or radiological technician pushes the handle 37 upwards, so as to cause the screen 28 to be wound on the takeup shaft 36 and stored in the storage box 30.

With the radiation detecting cassette 10A and the radiation image capturing system 12A according to the first embodiment, when the screen 28 is not being used to detect radiation 14 having passed through the patient 18, i.e., when the screen 28 is not used to capture a radiation image of the patient 18, the flexible radiation detector 40 is wound into a roll and stored in the storage box 30. When the screen 28 is used to detect radiation 14 having passed through the patient 18, i.e., when the screen 28 is used to capture a radiation image of the patient 18, the radiation detector 40 is pulled out of the storage box 30 and extended flatwise against the patient 18. Therefore, while the screen 28 is not being used to capture a radiation image of the patient 18, the radiation detector 40 is easily placed in storage. Further, when the screen 28 is used to capture a radiation image of the patient 18, the irradiated surface (the image-capturing surface) 32 of the radiation detector 40 can easily be kept in a flat condition against the patient 18.

The radiation detector 40 is incorporated in the screen 28, which can be stored in the storage box 30, and the proximal end of the screen 28 is coupled to the takeup shaft 36, whereas the distal end thereof is coupled to the weight bar 39. When the screen 28 is pulled out of the storage box 30, the screen 28 is extended vertically in a flat state under the weight of the weight bar 39. Therefore, the radiation image capturing system 12A according to the first embodiment is suitable for performing an upright image capturing process on the patient 18.

Since the battery 44, the cassette controller 46, and the transceiver 48 are housed in the weight bar 39, the screen 28 is reliably extended vertically in a flat state under the total weight of the weight bar 39, the battery 44, the cassette controller 46, and the transceiver 48. Consequently, the upright image capturing process can be accurately and reliably performed on the patient 18.

Furthermore, since the radiation detector 40 includes the scintillator 72, the TFT layer 74, and the photoelectric transducer layer 76, which are arranged successively in this order on the substrate 71, or in other words, since the radiation detector 40 includes the photoelectric transducer layer 76, the TFT layer 74, and the scintillator 72, which are arranged successively in this order from the irradiated surface 32, visible light generated by the scintillator 72 can efficiently be converted into electric signals by the photoelectric transducer layer 76. As a result, the radiation detector 40 can produce high quality radiation image information.

Furthermore, since signals are sent and received by way of wireless communications between the console 20, the radiation source 16, and the display device 22, no cables are required for transmitting and receiving signals therebetween, and hence cable-induced obstacles to operations performed by the doctor or the radiological technician do not occur. Therefore, the doctor and the radiological technician are able to perform their work smoothly and efficiently.

According to the first embodiment, moreover, radiation image information is captured when the doctor or the radiological technician turns on the image capturing switch. However, radiation image information may be captured when the doctor or the radiological technician operates the console 20.

Figure 6:
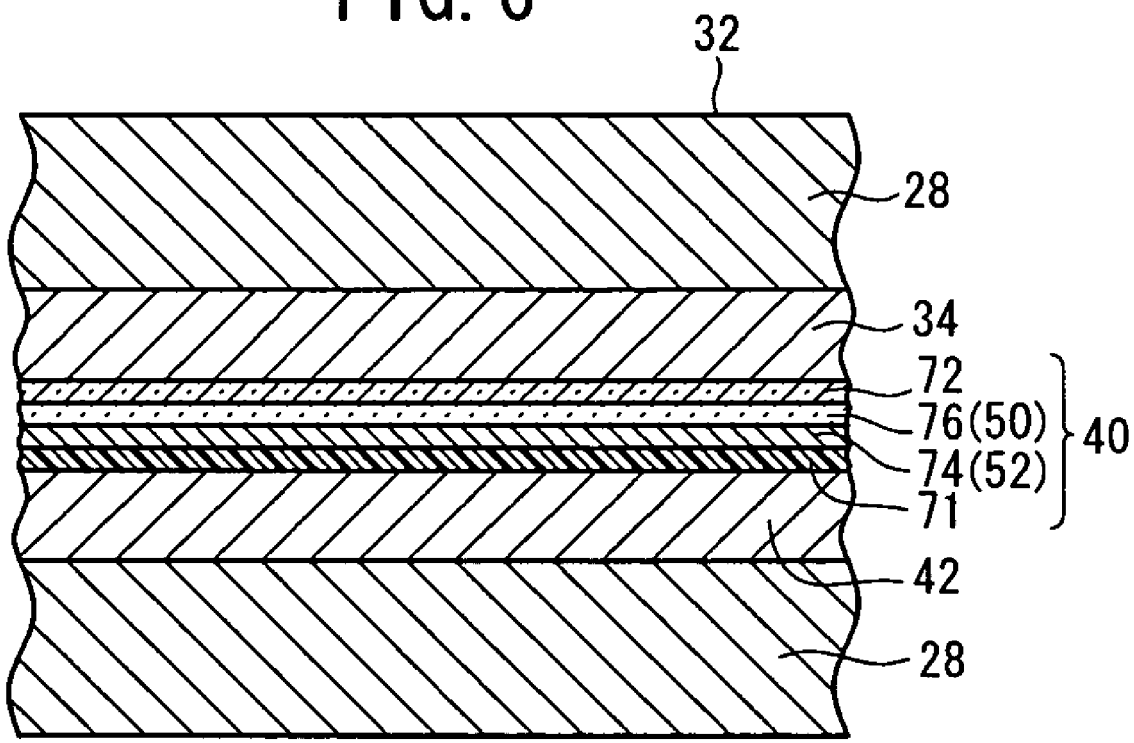
FIG. 6 is a cross-sectional view taken along line VI-VI of FIG. 3.

The radiation detecting cassette 10A according to the first embodiment may also be constructed according to the arrangement or modification shown in FIG. 6. According to the arrangement or modification shown in FIG. 6, the TFT layer 74, the photoelectric transducer layer 76, and the scintillator 72 are arranged successively in this order from the substrate 71 toward the irradiated surface 32. With the modified radiation detecting cassette 10A, visible light converted by the scintillator 72 can be converted into electric signals by the photoelectric transducer layer 76. The modified radiation detecting cassette 10A can thus offer the same advantages as those described above.

According to the first embodiment, the principles of the present invention may be applied to a direct-conversion-type radiation detecting apparatus, wherein the dose of applied radiation 14 is converted directly into electric signals by a photoelectric transducer layer, which comprises solid-state detectors made of a material such as amorphous selenium (a-Se).

According to the first embodiment, the radiation image capturing system 12A may employ a light readout type radiation detecting apparatus for acquiring radiation image information. Such a light readout type radiation detecting apparatus operates as follows. When radiation 14 is applied to a matrix of solid-state detecting devices, the solid-state detecting devices store an electrostatic latent image depending on the dose of applied radiation. For reading the stored electrostatic latent image, reading light is applied from a flexible organic EL (electroluminescent) panel or the like to a radiation detector in order to cause the radiation detector to generate an electric current representing the radiation image information. When erasing light is applied to the radiation detector, the radiation image information representing a residual electrostatic latent image is erased from the radiation detector, and the radiation detector can be reused (see Japanese Laid-Open Patent Publication No. 2000-105297).

According to the first embodiment, a stimulable phosphor panel for storing radiation energy representative of radiation image information, and thereafter emitting stimulated light representing the radiation image information upon exposure to stimulating light, may be used as a flexible radiation conversion panel.

When the radiation detecting cassette 10A is used in an operating room or the like, blood stains and other contaminants may be applied to the radiation detecting cassette 10A. The radiation detecting cassette 10A may comprise a water-resistant, sealed structure, so that the radiation detecting cassette 10A can be sterilized and cleaned to remove such blood stains and contaminants, thus enabling the radiation detecting cassette 10A to be used repeatedly.

The radiation detecting cassette 10A and an external device may communicate with each other by way of optical wireless communications using infrared rays or the like, rather than by means of usual wireless communications using radio waves.

Figure 7:
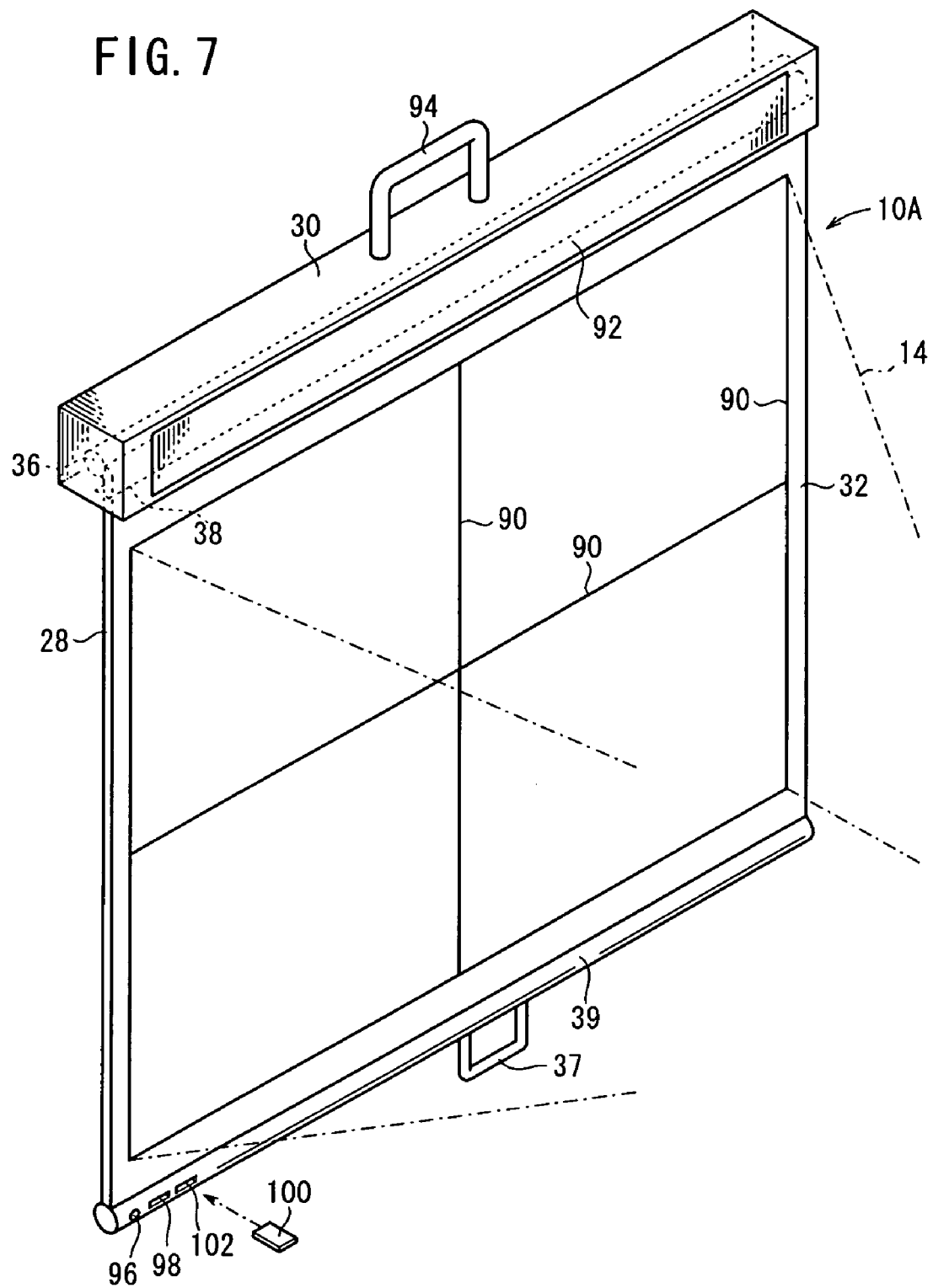
FIG. 7 is a perspective view of another arrangement of the radiation detecting apparatus according to the first embodiment.

FIG. 7 is a perspective view of another arrangement or modification of the radiation detecting cassette 10A according to the first embodiment.

The modified radiation detecting cassette 10A shown in FIG. 6 includes guide lines (markers) 90 drawn on the irradiated surface 32 of the screen 28, which serve as reference marks for an image capturing area and an image capturing position. Using such guide lines 90, the subject to be imaged, such as the patient 18, can be positioned with respect to the radiation detecting cassette 10A, and the range at which radiation 14 is to be applied to the radiation detecting cassette 10A can be determined, for thereby recording radiation image information within an appropriate image capturing area of the radiation detecting cassette 10A.

The radiation detecting cassette 10A also includes a display unit 92 disposed outside of the image capturing area thereof, i.e., on the storage box 30, for displaying various items of information concerning the radiation detecting cassette 10A. More specifically, the display unit 92 displays ID information of the patient 18 whose radiation image information is to be recorded in the radiation detecting cassette 10A, the number of times that the radiation detecting cassette 10A has been used, an accumulated exposure dose, the charged state (remaining power level) of the battery 44 housed in the radiation detecting cassette 10A, image capturing conditions for the radiation image information, and a positioning image representing the patient 18 positioned with respect to the radiation detecting cassette 10A, etc. The radiological technician can confirm the patient 18 based on the ID information displayed on the display unit 92, and also confirm in advance that the radiation detecting cassette 10A is in a usable state, to thereby position the desired area to be imaged of the patient 18 with respect to the radiation detecting cassette 10A based on the displayed positioning image, and capture optimum radiation image information in the radiation detecting cassette 10A.

The storage box 30 includes a handle 94 to be gripped by the user in order to handle and carry the radiation detecting cassette 10A with ease.

The weight bar 39 has an input terminal 96 for connection to an AC adapter, a USB (Universal Serial Bus) terminal 98, which serves as an interface means for sending and receiving information to and from an external device, and a card slot 102 for receiving a memory card 100 therein.

When the charge on the battery 44 housed in the radiation detecting cassette 10A is low, or when there is not enough time to charge the battery 44, an AC adapter is connected to the input terminal 96, so as to supply electric power from an external source for thereby making the radiation detecting cassette 10A immediately usable.

The USB terminal 98 or the card slot 102 can be used when the radiation detecting cassette 10A is unable to send and receive information to and from an external device, such as the console 20 or the like, by way of wireless communications. More specifically, when a USB cable connected to the external device is connected to the USB terminal 98, the radiation detecting cassette 10A can send and receive information to and from the external device by way of wired communications through the USB terminal 98 and the USB cable. Alternatively, the memory card 100 can be inserted into the card slot 102, whereby necessary information from the radiation detecting cassette 10A is recorded in the memory card 100. Thereafter, the memory card 100 is disconnected and connected to the external device in order to send the recorded information from the memory card 100 to the external device.

Figure 8:
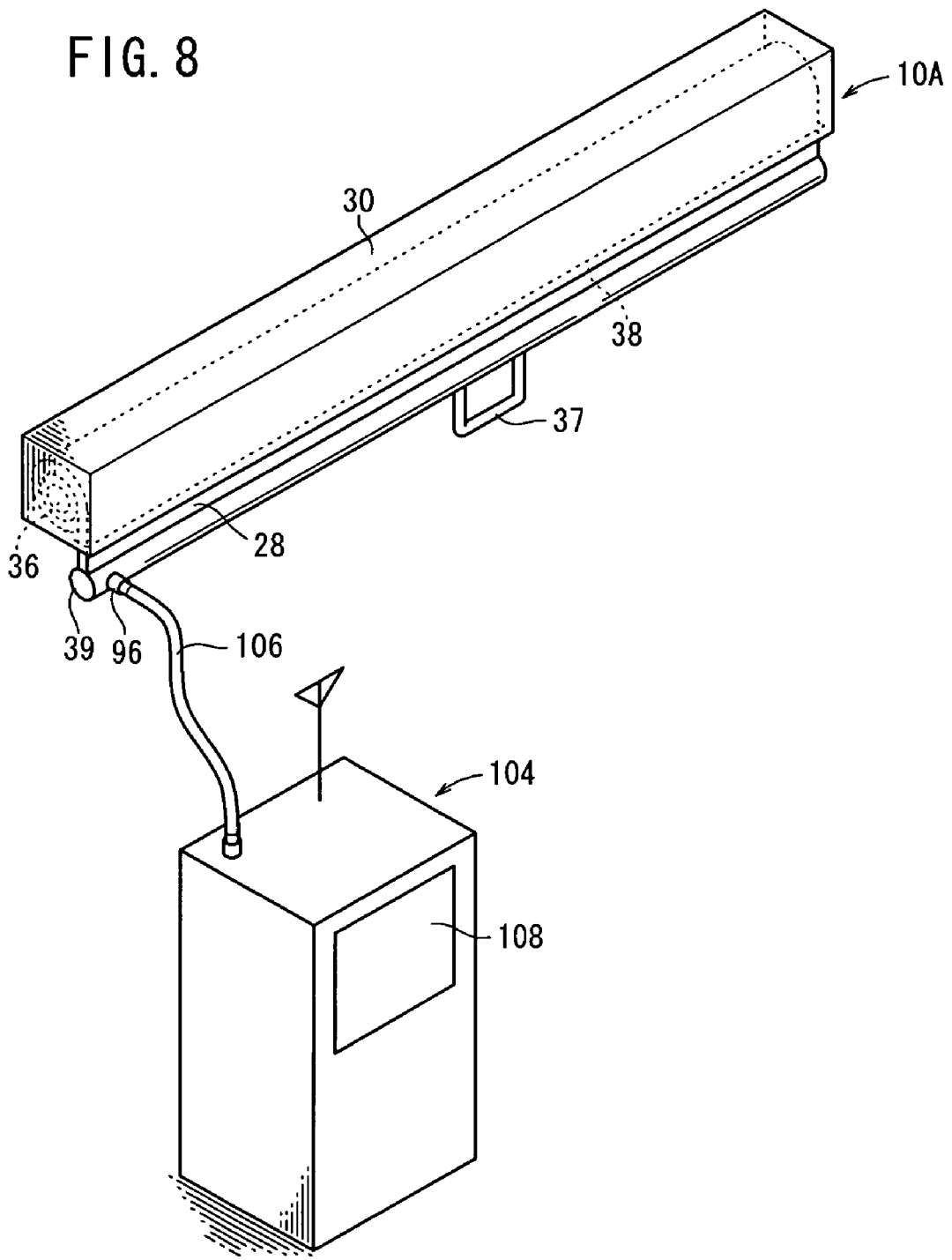
FIG. 8 is a perspective view of the radiation detecting apparatus according to the first embodiment, and a cradle for charging the radiation detecting apparatus.

FIG. 8 shows a cradle 104 for receiving the radiation detecting cassette 10A therein and for charging the battery 44 housed in the radiation detecting cassette 10A. The cradle 104 is positioned in an operating room or in another desired location in the hospital. The cradle 104 is not only capable of charging the battery 44, but may also have a wireless or wired communication function to send and receive necessary information to and from an external device, such as the RIS 24, the HIS 26, the console 20, or the like. The information sent from the cradle 104 may include radiation image information recorded in the radiation detecting cassette 10A, which is loaded in the cradle 104. Information is sent and received between the transceiver 48 and the cradle 104 by way of wireless communications.

The cradle 104 has a display unit 108 for displaying the charged state of the battery 44 housed in the radiation detecting cassette 10A, which is connected to the cradle 104, and other necessary information including radiation image information acquired from the radiation detecting cassette 10A.

As shown in FIG. 8, when the screen 28 is wound around the takeup shaft 36 and stored in the storage box 30, the cradle 104 charges the battery 44 (see FIG. 3). More specifically, when the cradle 104 detects that the screen 28 has been fully stored in the storage box 30, the cradle 104 can begin charging the battery 44, while stopping the supply of electric power from the battery 44 to the radiation detector 40, the cassette controller 46, and the transceiver 48. Alternatively, while the cradle 104 is charging the battery 44, the battery 44 can continue to supply electric power to the radiation detector 40, the cassette controller 46, and the transceiver 48.

Figure 9:
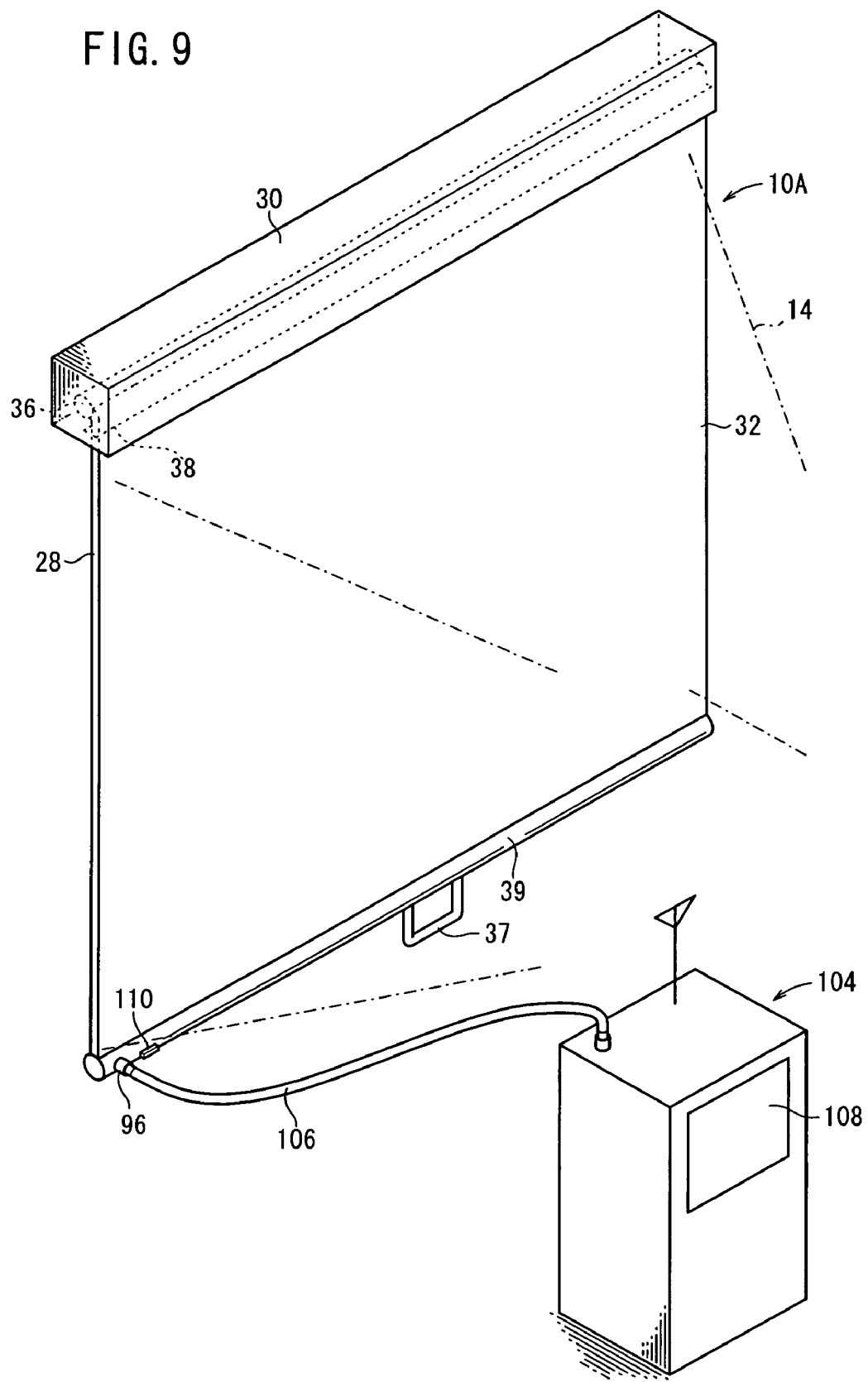
FIG. 9 is a perspective view of still another arrangement of the radiation detecting apparatus according to the first embodiment, and a cradle for charging the radiation detecting apparatus.

According to still another arrangement or modification of the radiation detecting apparatus 10A according to the first embodiment, as shown in FIG. 9, the weight bar 39 includes a power supply switch 110. The doctor or a radiological technician operates the power supply switch 110 in order to start or stop supplying electric power from the battery 44 to the radiation detector 40, the cassette controller 46, and the transceiver 48. When the power supply switch 110 is operated to stop supplying electric power from the battery 44 to the radiation detector 40, the cassette controller 46 and the transceiver 48, the cradle 104 begins charging the battery 44. With the arrangement shown in FIG. 9, it is possible to charge the battery 44, irrespective of whether the screen 28 has been stored in the storage box 30 or not. Alternatively, the cradle 104 can operate to charge the battery 44, irrespective of whether the power supply switch 110 is operated or not.

A plurality of cradles 104, each configured as shown in FIGS. 8 and 9, may be connected to a network, and the charged states of the batteries 44 housed in the radiation detecting cassettes 10A connected to the respective cradles 104 can be retrieved through the network, so that the user can confirm the locations of radiation detecting cassettes 10A whose batteries 44 are sufficiently charged, based on the retrieved charged states of the batteries 44.

A radiation detecting apparatus 10B according to a second embodiment of the present invention, and a radiation image capturing system 12B incorporating the radiation detecting apparatus 10B therein, will be described below with reference to FIGS. 10 through 15.

Those parts of the radiation detecting apparatus 10B and the radiation image capturing system 12B, which are identical to those of the radiation detecting apparatus 10A and the radiation image capturing system 12A (see FIGS. 1 through 9), are denoted by identical reference characters, and such features will not be described in detail below. This also holds true for the other embodiments.

The radiation detecting apparatus 10B and the radiation image capturing system 12B according to the second embodiment differ from the radiation detecting apparatus 10A and the radiation image capturing system 12A according to the first embodiment, in that a radiation detecting cassette 122B including the radiation detector (radiation conversion panel) 40 is stored in a cassette storage pouch (storage body) 120B, which is permeable to radiation 14 while blocking external light.

With the radiation detecting apparatus 10A and the radiation image capturing system 12A according to the first embodiment, the radiation detecting apparatus 10A functions as a radiation detecting cassette which includes the radiation detector 40. On the other hand, with the radiation detecting apparatus 10B and the radiation image capturing system 12B according to the second embodiment, the radiation detecting apparatus 10B comprises the radiation detecting cassette 122B and the cassette storage pouch 120B, which stores the radiation detecting cassette 122B therein.

As described above, the radiation detecting apparatus 10B and the radiation image capturing system 12B according to the second embodiment differ basically from the radiation detecting apparatus 10A and the radiation image capturing system 12A according to the first embodiment. Specific structural details of the radiation detecting apparatus 10B and the radiation image capturing system 12B according to the second embodiment will be described below.

Figure 11A:
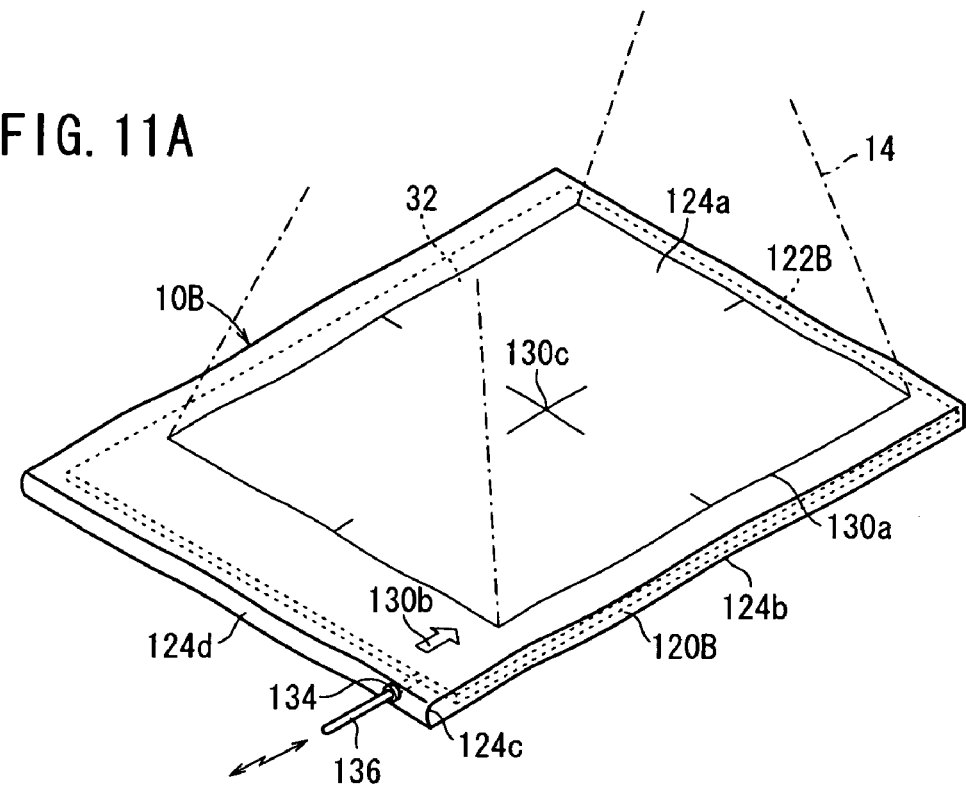
FIGS. 11A and 11B are perspective views of the radiation detecting apparatus shown in FIG. 10.
Figure 11B:
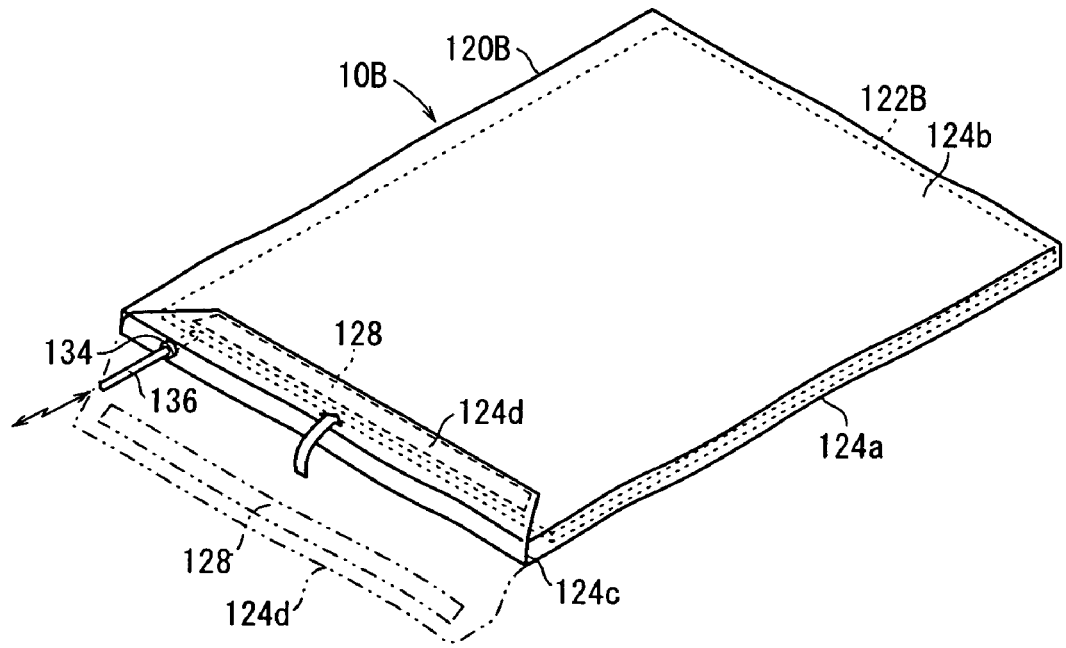
Figure 12:
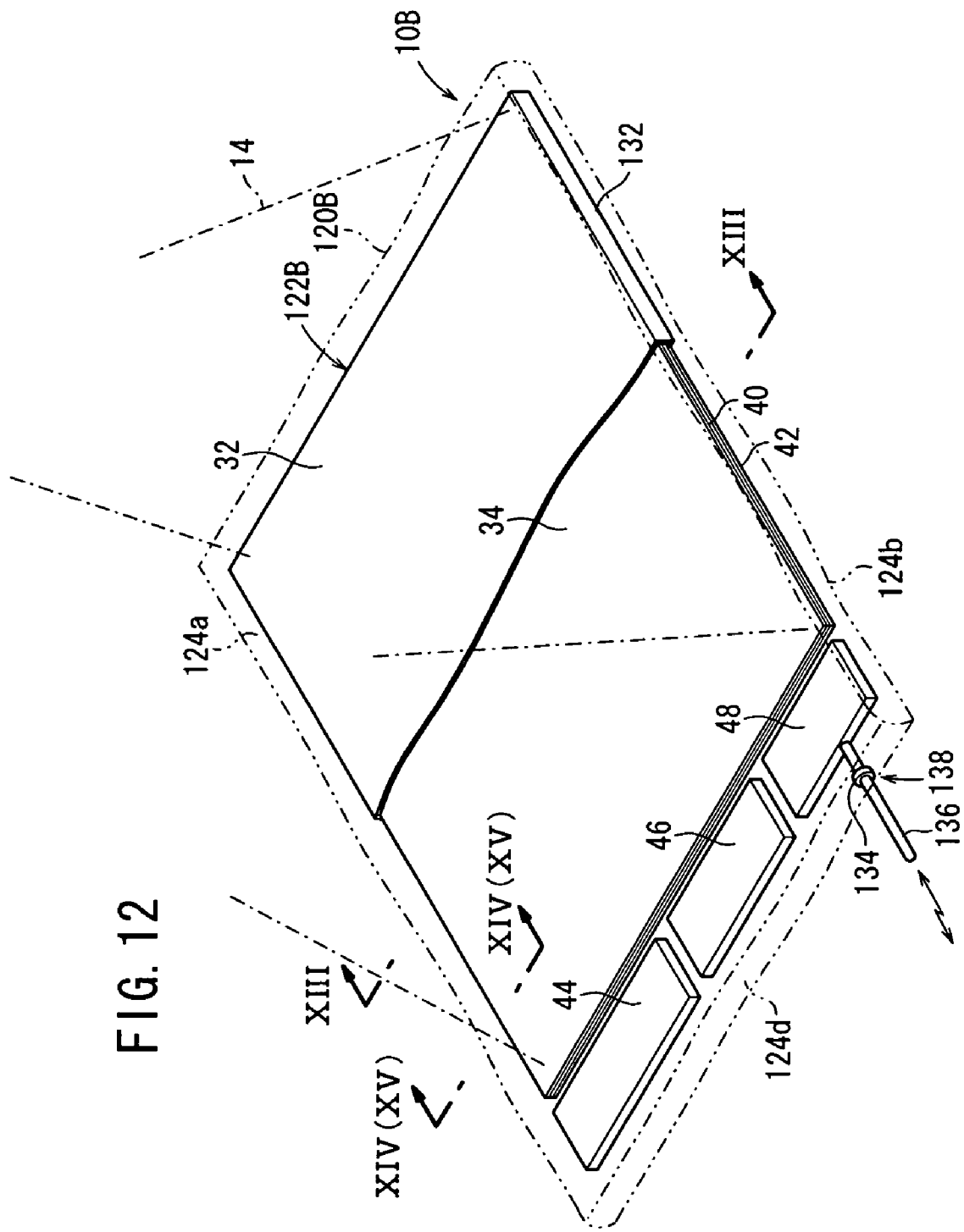
FIG. 12 is a perspective view, partially cut away, of the radiation detecting apparatus shown in FIG. 10.

As shown in FIGS. 10 through 12, the radiation detecting cassette 10B includes the cassette storage pouch 120B, which is permeable to radiation 14 while also blocking external light, and the radiation detecting cassette 122B in which the cassette storage pouch 120B is accommodated, and which is equipped with the radiation detector 40 that detects radiation having passed through the patient 18.

As shown in FIGS. 11A through 13, the cassette storage pouch 120B serves as a cover for storing the radiation detecting cassette 122B therein. The cassette storage pouch 120B is made of a material that blocks external light, is permeable to the radiation 14, is resistant to humidity, blocks electromagnetic waves apart from the radiation 14, e.g., radiation emitted from radiation sources different from the radiation source 16, and is flexible. The cassette storage pouch 120B having the aforementioned properties may comprise a light-impermeable pouch made of aluminum, for example. The cassette storage pouch 120B is sterilized in order to prevent body fluids, blood, and other contaminants from entering into the radiation detecting cassette 122B in facilities such as hospitals, and also to protect the patient 18 against hospital-acquired infections. The radiation detecting cassette 122B normally is disposable after a single use thereof.

FIG. 11A is a perspective view of the radiation detecting apparatus 10B showing a front surface 124a thereof. FIG. 11B is a perspective view of the radiation detecting apparatus 10B showing a rear surface 124b thereof.

The radiation detecting cassette 122B has an opening 124c defined in one end thereof for insertion of the radiation detecting cassette 122B. The opening 124c can be closed by a lid 124d, which extends from the front surface 124a that faces the irradiated surface 32 of the radiation detecting cassette 122B. The lid 124d can be attached firmly to the rear surface 124b, which is opposite to the front surface 124a, by means of a sealing tape 128, for thereby sealing the radiation detecting cassette 122B within the cassette storage pouch 120B.

The front surface 124a of the cassette storage pouch 120B is printed with a frame (mark) 130a, indicating that the front surface 124a faces the irradiated surface 32 of the radiation detecting cassette 122B and representing an image capturing area, a mark 130c representing the center of the image capturing area, and a mark 130b representing the direction in which the radiation detecting cassette 122B can be inserted into the cassette storage pouch 120B. The marks 130a, 130b, 130c are printed using a material permeable to radiation 14. The mark 130b is effective in preventing the doctor or a radiological technician from inserting the radiation detecting cassette 122B into the cassette storage pouch 120B in a wrong direction.

The radiation detecting cassette 122B that is stored in the cassette storage pouch 120B comprises a flexible sheet-like cassette. As shown in FIGS. 11A through 14, the radiation detecting cassette 122B includes a flexible case 132 permeable to radiation 14. Before the radiation detecting cassette 122B is inserted into the cassette storage pouch 120B, the radiation detecting cassette 122B is wound into a roll and stored in a storage box, not shown. When the radiation detecting cassette 122B is inserted into the cassette storage pouch 120B, the radiation detecting cassette 122B is spread out substantially flatwise for use under the patient 18. The case 132 should preferably be made of the same material as the screen 28 (see FIGS. 2A through 4, and FIGS. 6 through 9) of the radiation detecting apparatus 10A according to the first embodiment.

As with the screen 28, the case 132 houses therein the grid 34, the radiation detector 40, and the lead sheet 42, which are successively arranged in this order from the irradiated surface (image-capturing surface) 32 of the case 132 that faces toward the patient 18. The grid 34, the radiation detector 40, and the lead sheet 42 are flexible. The irradiated surface 32 of the case 132 may also be constructed as the grid 34. As shown in FIG. 12, the battery 44, the cassette controller 46, and the transceiver 48 also are housed within the case 132.

A rod-shaped antenna (first antenna) 136 is connected to the transceiver 48. When the radiation detecting cassette 122B is stored in the cassette storage pouch 120B, the rod-shaped antenna 136 projects outside of the cassette storage pouch 120B through a tubular electric insulator 134, which is mounted in a hole defined in the lid 124d of the cassette storage pouch 120B. The antenna 136 and the transceiver 48 jointly make up a wireless communication means 138.

As described above, the cassette storage pouch 120B blocks electromagnetic waves that differ from the radiation 14. Therefore, the wireless communication means 138 can send and receive signals including information concerning the radiation 14 detected by the radiation detector 40 between the antenna 136 and the console 20 by way of wireless communications only when the antenna 136 projects outside of the cassette storage pouch 120B through the tubular electric insulator 134.

The wireless communication means 138 sends cassette ID information stored in the cassette ID memory 86 and radiation image information stored in the image memory 84 to the console 20 by way of wireless communications.

The electric insulator 134 is provided to prevent electric contact between the material (aluminum) of the cassette storage pouch 120B and the antenna 136.

Figure 13:
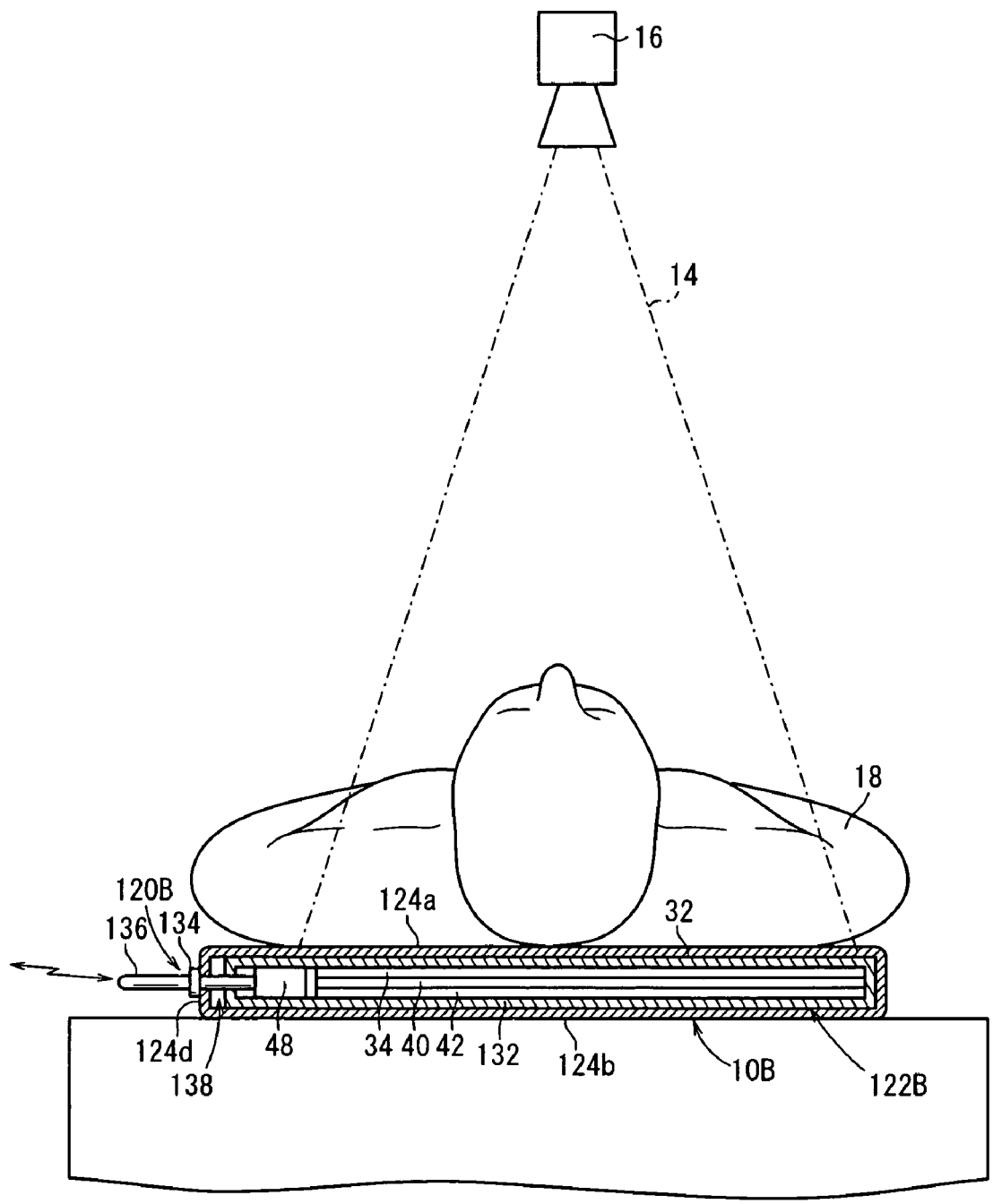
FIG. 13 is a cross-sectional view taken along line XIII-XIII of FIG. 12.

The antenna 136 can be extended and contracted through the transceiver 48 and the electric insulator 134, i.e., in the left and right directions as shown in FIG. 13. When the radiation detecting cassette 122B is inserted into the cassette storage pouch 120B, the antenna 136 is extended from the transceiver 48 by a certain length, which is small enough so as not to present an obstacle to subsequent closing of the opening 124c with the lid 124d. Then, the opening 124c is closed by the lid 124d, and thereafter the antenna 136 is further extended a required length to enable wireless communications between the antenna 136 and the console 20. In this manner, signals can be sent and received between the antenna 136 and the console 20 by way of wireless communications. The antenna 136, which can be extended and contracted, may be replaced with a foldable antenna.

The position where the electric insulator 134 is located is not limited to the lid 124d as shown in FIGS. 11A through 13. The electric insulator 134 may be located in any position where it does not obstruct application of radiation 14 and which allows signals to be sent to and received from the console 20 by way of wireless communications. For example, the electric insulator 134 may be mounted on a side edge of the cassette storage pouch 120B, and the antenna 136 may project out of the cassette storage pouch 120B through the side edge thereof.

The electric insulator 134 may be dispensed with, and the edge of the hole defined in the lid 124d and nearby regions thereof may be covered with an electric insulating material. Such an electric insulating material offers the same advantages as those of the electric insulator 134.

The radiation detecting apparatus 10B and the radiation image capturing system 12B according to the second embodiment are basically constructed as described above. Operations of the radiation detecting apparatus 10B and the radiation image capturing system 12B will be described below.

For capturing radiation image information of the patient 18 when the doctor performs a surgical operation on the patient 18 in an operating room, when the doctor examines the patient 18, or when the doctor goes on rounds in the hospital, after the patient information and the image capturing conditions have been registered, the doctor or a radiological technician removes the rolled radiation detecting cassette 122B from the storage box (not shown) and spreads the radiation detecting cassette 122B flatwise. Then, the doctor or radiological technician detaches the lid 124d of the cassette storage pouch 120B from the rear surface 124b. While keeping the opening 124c thereof open, the doctor or radiological technician inserts the radiation detecting cassette 122B into the cassette storage pouch 120B along the direction indicated by the mark 130b. Then, the doctor or radiological technician pulls the antenna 136 from the radiation detecting cassette 122B by a length, which is small enough not to present an obstacle to subsequent closing of the opening 124c with the lid 124d, and threads the tip end of the antenna 136 through the electric insulator 134. Thereafter, the doctor or radiological technician closes the opening 124c with the lid 124d, thereby sealing the radiation detecting cassette 122B in the cassette storage pouch 120B. Then, the doctor or radiological technician pulls the antenna 136 a required length to enable wireless communications between the antenna 136 and the console 20.

Next, the doctor or radiological technician places the radiation detecting apparatus 10B between the patient 18 and the bed, with the front surface 124a (the irradiated surface 32) facing the radiation source 16. After having moved the radiation source 16 to a position facing the radiation detecting apparatus 10B, the doctor or radiological technician operates an image capturing switch, not shown, of the radiation source 16 in order to start capturing a radiation image of the patient 18, in the same manner as the first embodiment.

In the second embodiment, radiation 14 that has passed through the patient 18 passes through the front surface 124a of the cassette storage pouch 120B. Radiation 14 is applied to the grid 34 of the radiation detecting cassette 122B, which removes scattered rays from the radiation 14. Then, the radiation 14 is applied to the radiation detector 40, which converts the radiation 14 into radiation image information. The radiation image information is stored in the image memory 84, and then is sent from the transceiver 48 through the antenna 136 to the console 20 by way of wireless communications.

After having captured a radiation image of the patient 18, the doctor or radiological technician pushes the antenna 136 through the electric insulator 134 back into the radiation detecting cassette 122B. The doctor or radiological technician detaches the lid 124d from the rear surface 124b, removes the radiation detecting cassette 122B from the cassette storage pouch 120B through the opening 124c, winds the case 132 into a roll, and stores the radiation detecting cassette 122B in the storage box. The radiation detecting cassette 122B, from which the cassette storage pouch 120B has been removed, is discarded after the image capturing process, i.e., after a single use thereof.

With the radiation detecting apparatus 10B and the radiation image capturing system 12B according to the second embodiment, as described above, the cassette storage pouch 120B blocks external light while being permeable to radiation 14. Therefore, the cassette storage pouch 120B reliably shields the radiation detecting cassette 122B (the radiation detector 40) from external light, thus allowing the radiation detecting cassette 122B to acquire radiation image information highly accurately.

As described above, the cassette storage pouch 120B is made of a material that blocks external light, is permeable to radiation 14, is resistant to humidity, blocks electromagnetic waves that differ from the radiation 14, e.g., radiation emitted from radiation sources different from the radiation source 16, and is flexible. For example, the cassette storage pouch 120B may comprise a light-impermeable pouch made of aluminum. The cassette storage pouch 120B is effective in preventing body fluids, blood, and other contaminants from entering into the radiation detecting cassette 122B, and also protects the patient 18 against hospital-acquired infections. Since the cassette storage pouch 120B is capable of reliably preventing noise caused by external light, as well as noise caused by electromagnetic waves different from the radiation 14, from being added to the radiation image information, the radiation detecting cassette 122B can produce radiation image information highly accurately. Furthermore, since it is flexible, the cassette storage pouch 120B can be handled with ease.

Since the cassette storage pouch 120B blocks external light from reaching the scintillator 72 and the photoelectric transducer layer 76, the radiation detecting apparatus 10B is more effective than the radiation detecting apparatus disclosed in Japanese Laid-Open Patent Publication No. 2003-070776 in preventing noise caused by external light from being added to the radiation image information.

Inasmuch as the radiation detecting cassette 122B is flexible, the radiation detecting cassette 122B can be wound into a roll and stored in the storage box or the like. When the radiation detecting cassette 122B is stored in the cassette storage pouch 120B, the radiation detecting cassette 122B is extended flatwise. Therefore, the radiation detecting apparatus 10B can be handled with utmost ease.

According to the second embodiment, furthermore, the antenna 136 is extended from the transceiver 48 of the radiation detecting cassette 122B and outside of the cassette storage pouch 120B through the electric insulator 134, for sending and receiving signals to and from the console 20 by way of wireless communications. Therefore, even when the radiation detecting cassette 122B is stored inside the cassette storage pouch 120B, signals can be reliably sent and received to and from the console 20 by way of wireless communications.

Figure 15:
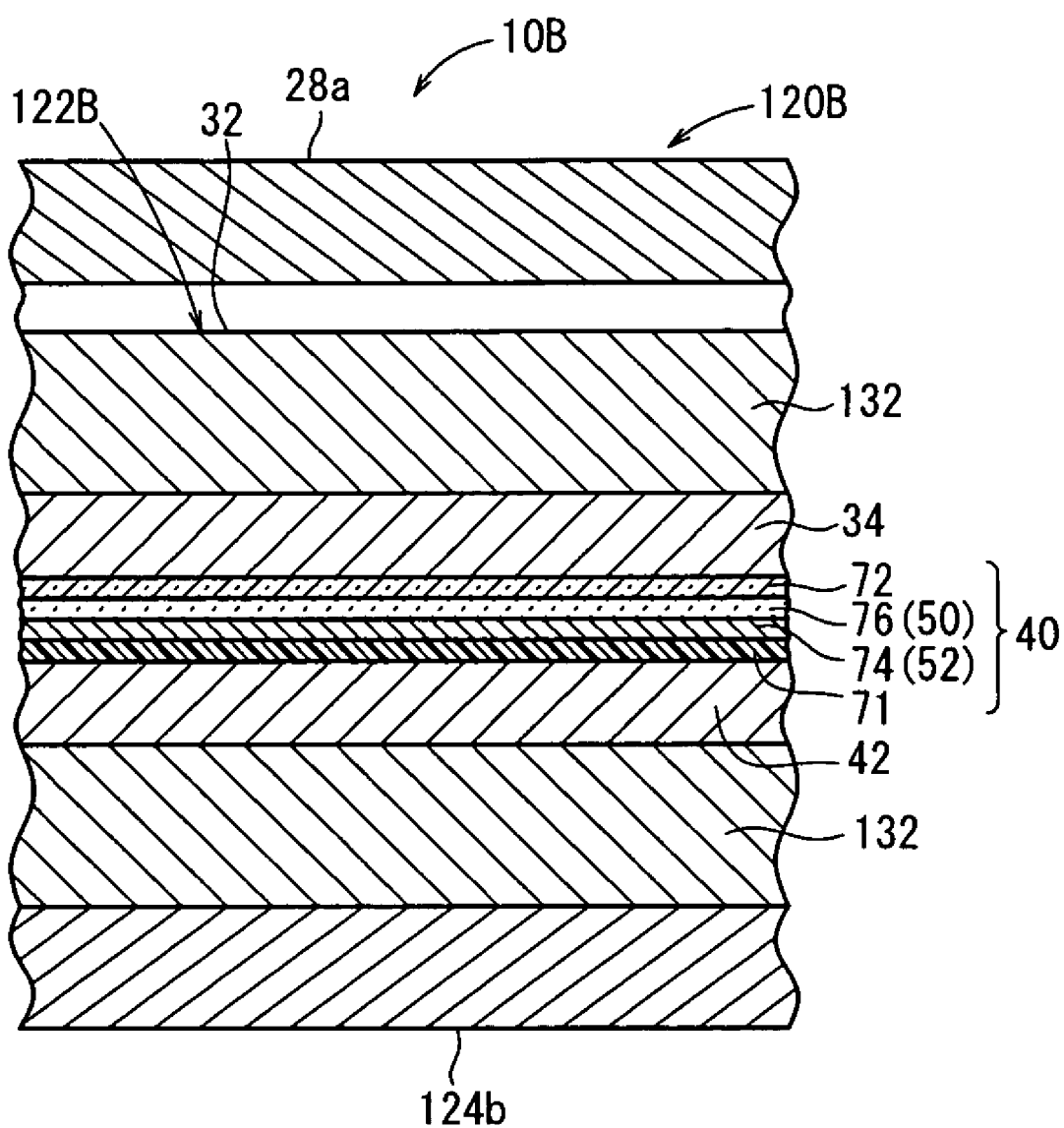
FIG. 15 is a cross-sectional view taken along line XV-XV of FIG. 12.

The radiation detecting apparatus 10B according to the second embodiment may include the arrangement or modification shown in FIG. 15. According to the arrangement or modification shown in FIG. 15, the TFT layer 74, the photoelectric transducer layer 76, and the scintillator 72 are successively arranged in this order from the substrate 71 toward the irradiated surface 32, similar to the arrangement or modification shown in FIG. 6. The modified radiation detecting apparatus 10B can thus offer the advantages of the second embodiment, which have been described above, while also offering the same advantages as those of the arrangement or modification shown in FIG. 6.

According to the second embodiment, a stimulable phosphor panel for storing radiation energy representative of the radiation image information, and thereafter emitting stimulated light representative of the radiation image information upon exposure to stimulating light, may be used as a flexible radiation conversion panel.

According to the second embodiment, the radiation detecting cassette 122B, which comprises the radiation detector 40 housed in the sheet-like case 132, may be replaced with a cassette comprising the radiation detector 40 housed in a rectangular casing. Such a cassette also offers the same advantages provided by housing the cassette in the cassette storage pouch 120B.

Instead of the cassette storage pouch 120B, the radiation detecting cassette 122B may be housed in a rectangular casing, which blocks external light, is permeable to radiation 14, is resistant to humidity, and blocks electromagnetic waves that differ from the radiation 14. The rectangular casing is not flexible and hence does not offer the advantages that result from a flexible casing, but still offers advantages due to the fact that the rectangular casing blocks external light, is permeable to radiation 14, is resistant to humidity, and blocks electromagnetic waves that differ from the radiation 14.

Figure 14:
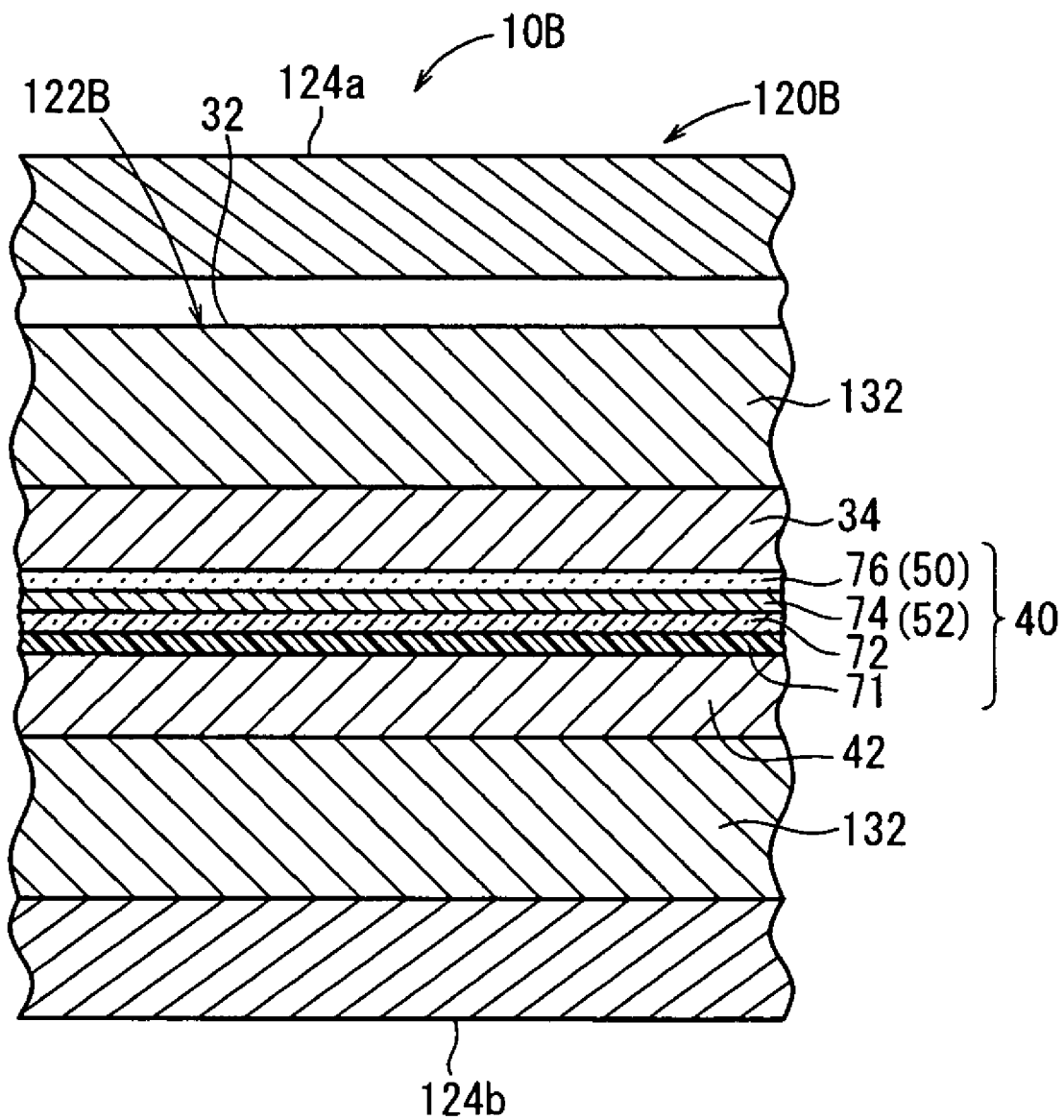
FIG. 14 is a cross-sectional view taken along line XIV-XIV of FIG. 12.

According to the second embodiment, as shown in FIGS. 14 and 15, the scintillator 72, the TFT layer 74, and the photoelectric transducer layer 76 are combined integrally in the radiation detector 40 of the radiation detecting cassette 122B. However, the grid 34, the scintillator 72, the TFT layer 74, the photoelectric transducer layer 76, the lead sheet 42, and the unit comprising the battery 44, the cassette controller 46 and the transceiver 48 may be constructed separately. Then, when housed in the cassette storage pouch 120B, the grid 34, the scintillator 72, the TFT layer 74, the photoelectric transducer layer 76, the lead sheet 42, and the unit jointly make up the radiation detecting cassette 122B. The cassette storage pouch 120B may have a plurality of pocket-like receptacles, so that after the grid 34, the scintillator 72, the TFT layer 74, the photoelectric transducer layer 76, the lead sheet 42, and the unit have been stored respectively in the pocket-like receptacles, the unit, the scintillator 72, the TFT layer 74, and the photoelectric transducer layer 76 may be connected by cables, thereby making up the radiation detecting cassette 122B.

In this case, when the cassette storage pouch 120B becomes no longer usable, the radiation detecting cassette 122B stored in the cassette storage pouch 120B may be removed and used repeatedly in a new cassette storage pouch 120B. Since the components are disposed separately from each other, the scintillator 72 may easily be replaced with another scintillator, e.g., a high-definition-type scintillator or a high-sensitivity-type scintillator, having different specifications established under different image capturing conditions. More specifically, since the scintillator 72 is a relatively expensive component, the radiation detecting apparatus 10B may be made lower in cost by repeatedly using the scintillator 72, or replacing it with another scintillator 72 depending on different image capturing conditions.

A radiation detecting apparatus 10C according to a third embodiment of the present invention and a radiation image capturing system 12C incorporating the radiation detecting apparatus 10C will be described below with reference to FIGS. 16 through 19.

The radiation detecting apparatus 10C and the radiation image capturing system 12C according to the third embodiment differ from the radiation detecting apparatus 10B and the radiation image capturing system 12B according to the second embodiment (see FIGS. 10 through 15), in that a printed antenna (second antenna) 142 is printed on an electric insulation layer 140 on the rear surface 124b of the cassette storage pouch 120C. Also, a cable 144 from the transceiver 48 and a cable 146 connected to the printed antenna 142 are connected to each other by a connector 148 connected to the cable 144 and a connector 150 connected to the cable 146, for allowing signals to be sent and received between the wireless communication means 138 and the console 20 by way of wireless communications.

More specifically, with the radiation detecting apparatus 10B and the radiation image capturing system 12B according to the second embodiment, signals are sent and received between the wireless communication means 138 and the console 20 by way of wireless communications using a rod-shaped antenna 136. However, with the radiation detecting apparatus 10C and the radiation image capturing system 12C according to the third embodiment, signals are sent and received between the wireless communication means 138 and the console 20 by way of wireless communications using the printed antenna 142.

The radiation detecting apparatus 10C and the radiation image capturing system 12C according to the third embodiment differ basically from the radiation detecting apparatus 10B and the radiation image capturing system 12B according to the second embodiment, as described above. Specific structural details of the radiation detecting apparatus 10C and the radiation image capturing system 12C according to the third embodiment will be described below.

As shown in FIGS. 16 through 19, a cassette storage pouch 120C differs from the cassette storage pouch 120B (see FIGS. 10 through 15), in that the printed antenna 142 is printed on an electric insulation layer 140 on the rear surface 124b, the cable 146 and the connector 150 are connected to the printed antenna 142, and the cassette storage pouch 120C does not contain the electric insulator 134. A radiation detecting cassette 122C differs from the radiation detecting cassette 122B, in that instead of the antenna 136, the cable 144 and the connector 148 are connected to the transceiver 48.

While the lid 124d of the cassette storage pouch 120C is kept detached from the rear surface 124b, the doctor or a radiological technician inserts the radiation detecting cassette 122B into the cassette storage pouch 120C along the direction indicated by the mark 130b. Then, the doctor or radiological technician connects the connector 148 connected to the cable 144 from the transceiver 48 and the connector 150 connected to the cable 146 from the printed antenna 142 to each other. Thereafter, the doctor or radiological technician closes the opening 124c with the lid 124d, thereby sealing the radiation detecting cassette 122C in the cassette storage pouch 120C. At this time, signals can be sent and received between the wireless communication means 138 and the console 20 by way of wireless communications, and a radiation image of the patient 18 can be captured by the radiation detecting apparatus 10C.

Figure 17A:
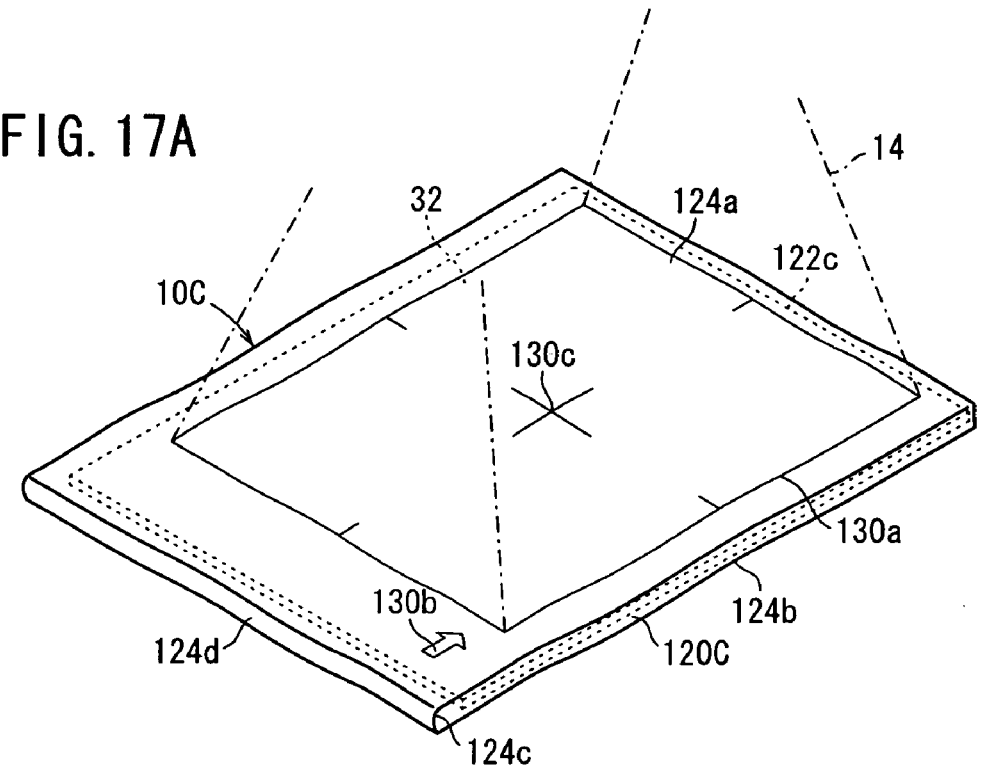
FIGS. 17A and 17B are perspective views of the radiation detecting apparatus shown in FIG. 16.
Figure 17B:
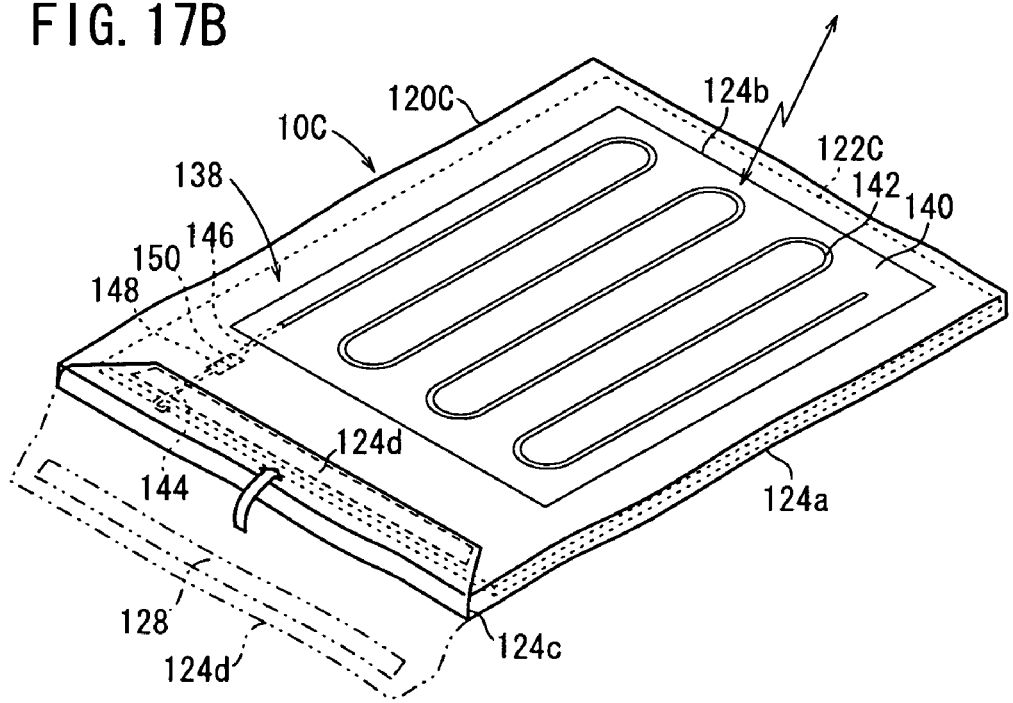
Figure 18:
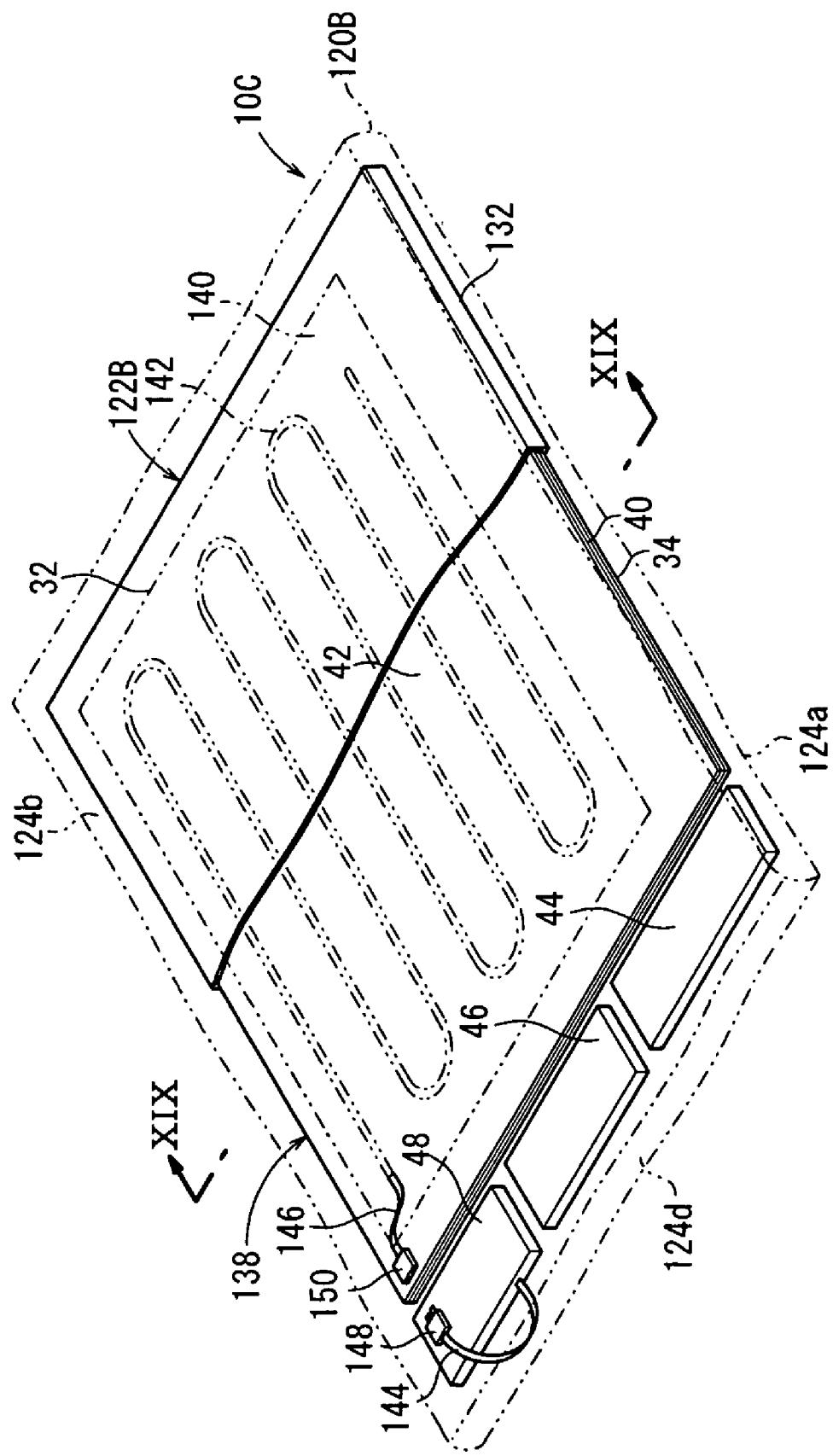
FIG. 18 is a perspective view, partially cut away, of the radiation detecting apparatus shown in FIG. 16.
Figure 19:
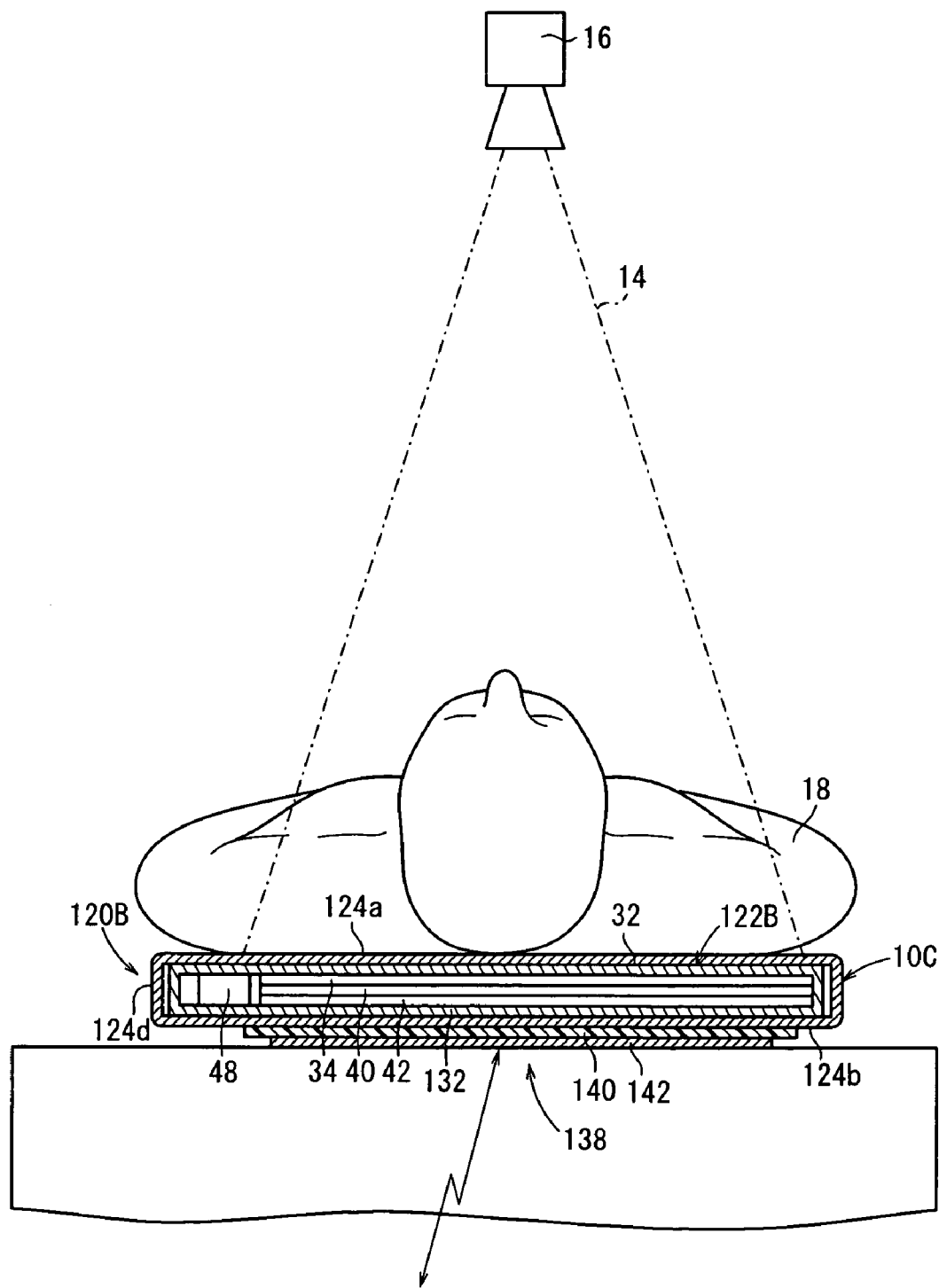
FIG. 19 is a cross-sectional view taken along line XIX-XIX of FIG. 18.

The electric insulation layer 140 is disposed on the rear surface 124b of the cassette storage pouch 120C so as to provide electric insulation between the printed antenna 142 and the material (aluminum) of the cassette storage pouch 120C. The position where the printed antenna 142 and the electric insulation layer 140 are located is not limited to the rear surface 124b, as shown in FIGS. 17B, 18, and 19. The printed antenna 142 and the electric insulation layer 140 may be located in any position where they do not obstruct application of radiation 14, and which allows signals to be sent to and received from the console 20 by way of wireless communications. For example, the printed antenna 142 and the electric insulation layer 140 may be disposed on the lid 124d, or on a side edge of the cassette storage pouch 120C.

As described above, with the radiation detecting apparatus 10C and the radiation image capturing system 12C according to the third embodiment, when the connector 148 connected to the cable 144 from the transceiver 48 and the connector 150 connected to the cable 146 from the printed antenna 142 are connected to each other, the connectors 148, 150 allow signals to be sent and received between the wireless communication means 138 and the console 20 by way of wireless communications. The radiation detecting apparatus 10C and the radiation image capturing system 12C according to the third embodiment offer the same advantages as the radiation detecting apparatus 10B and the radiation image capturing system 12B according to the second embodiment. Further, since the electric insulator 134 is not required, the cassette storage pouch 120C is more effective in blocking external light, more resistant to humidity, and more effective in blocking electromagnetic waves that differ from the radiation 14.

The second and third embodiments may have the following arrangements:

When the radiation detecting apparatus 10B, 10C are used in an operating room or the like, blood stains and other contaminants may be applied to the radiation detecting apparatus 10B, 10C. The cassette storage pouches 120B, 120C may be of a water-resistant, sealed structure, so that the cassette storage pouches 120B, 120C can be sterilized and cleaned in order to remove such blood stains and contaminants, thereby enabling the radiation detecting apparatus 10B, 10C to be used repeatedly.

The radiation detecting apparatus 10B, 10C and an external device may communicate with each other by way of optical wireless communications using infrared rays or the like, rather than by usual wireless communications using radio waves.

Figure 20:
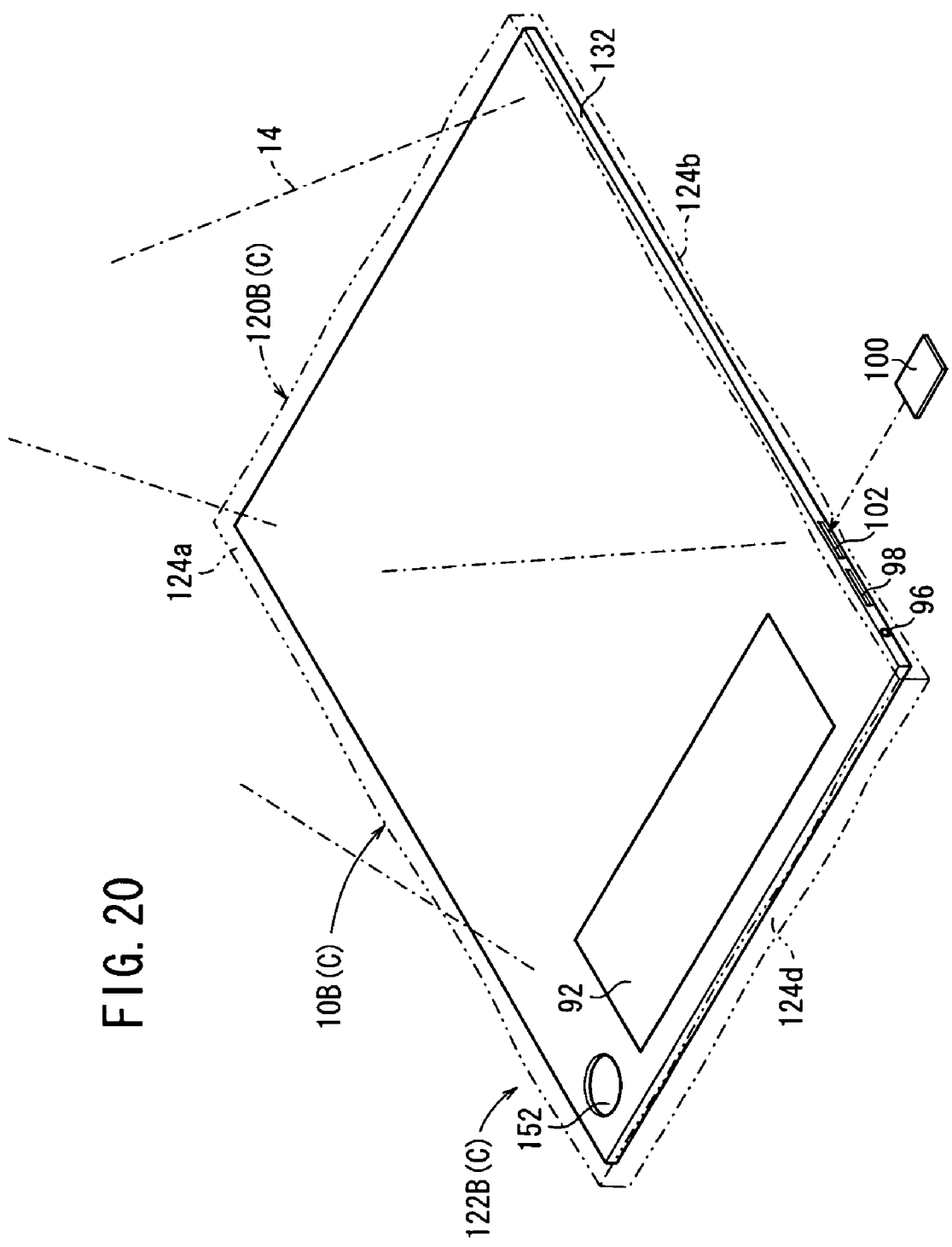
FIG. 20 is a perspective view of another arrangement of the radiation detecting apparatus according to the second and third embodiments.

The radiation detecting cassettes 122B, 122C may consist of another arrangement or modification, as shown in FIG. 20, similar to the case of the arrangement or modification shown in FIG. 7.

As shown in FIG. 20, each of the radiation detecting cassettes 122B, 122C has a display unit 92 disposed outside of the image capturing area thereof, for displaying various items of information concerning the radiation detecting cassettes 122B, 122C. More specifically, the display unit 92 displays ID information of the patient 18 whose radiation image information is recorded in the radiation detecting cassettes 122B, 122C, the number of times that the radiation detecting cassettes 122B, 122C have been used, an accumulated exposure dose, a charged state (remaining power level) of the battery 44 housed in the radiation detecting cassettes 122B, 122C, and image capturing conditions for the radiation image information, etc. The radiological technician can confirm the identity of the patient 18 based on the ID information displayed on the display unit 92, and also confirm in advance that the radiation detecting cassettes 122B, 122C are in a usable state, so as to capture optimum radiation image information in the radiation detecting cassettes 122B, 122C.

The case 132 has a hole 152 defined therein. A string, not shown, is threaded through the hole 152 and fastened to the case 132 so as to make the radiation detecting cassettes 122B, 122C easy to handle and carry.

Each of the radiation detecting cassettes 122B, 122C also has an input terminal 96 for connection to an AC adapter, a USB terminal 98, and a card slot 102 for receiving a memory card 100 therein. Therefore, the radiation detecting cassettes 122B and 122C offer the same advantages as the radiation detecting cassette 10A shown in FIG. 7.

Figure 21:
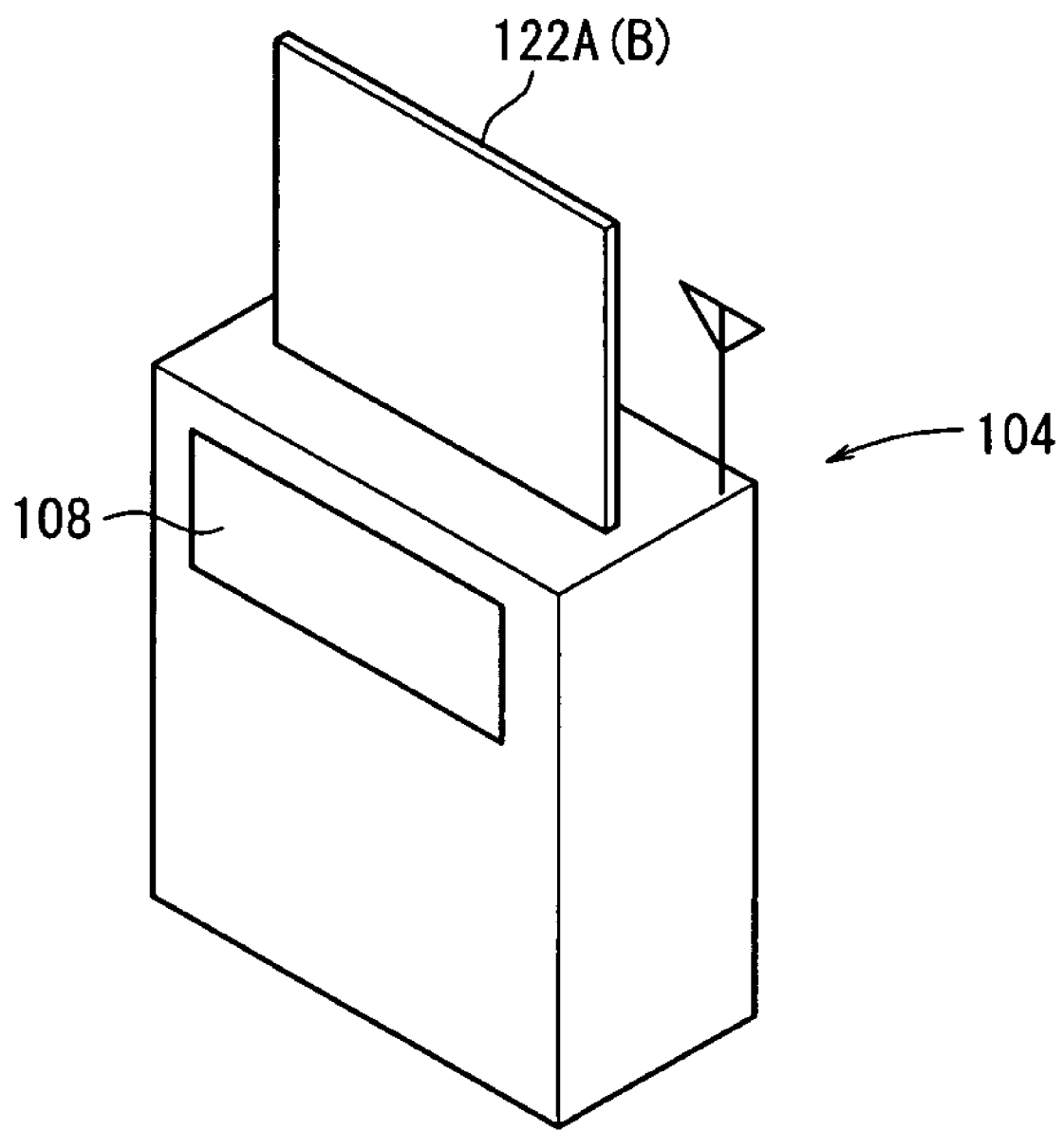
FIG. 21 is a perspective view of a cradle for charging the radiation detecting apparatus according to the second and third embodiments.

FIG. 21 shows a cradle 104 for receiving each of the radiation detecting cassettes 122B, 122C therein for charging the battery 44 housed in the radiation detecting cassettes 122B, 122C. The cradle 104 is positioned in an operating room or another desired location in the hospital. The cradle 104 not only is capable of charging the battery 44, but also may have a wireless or wired communication function to send and receive necessary information to and from an external device, such as the RIS 24, the HIS 26, the console 20, or the like. The information sent from the cradle 104 may include radiation image information, which is recorded in each of the radiation detecting cassettes 122B, 122C loaded in the cradle 104.

The cradle 104 includes a display unit 108 for displaying a charged state of the battery 44 housed in each of the radiation detecting cassettes 122B, 122C that are loaded in the cradle 104, and other necessary information including radiation image information acquired from each of the radiation detecting cassettes 122B, 122C loaded in the cradle 104.

A plurality of cradles 104 may be connected to a network, wherein charged states of the batteries 44 of the radiation detecting cassettes 122B, 122C loaded in the cradles 104 is retrieved through the network, so that the user can confirm locations of radiation detecting cassettes 122B, 122C having batteries 44 therein that are sufficiently charged, based on the retrieved charged states of such batteries 44.

A radiation detecting apparatus 10D according to a fourth embodiment of the present invention and a radiation image capturing system 12D incorporating the radiation detecting apparatus 10D will be described below with reference to FIGS. 22 through 30.

The radiation detecting apparatus 10D and the radiation image capturing system 12D according to the fourth embodiment differ from the radiation detecting apparatus 10A, 10B, 10C and the radiation image capturing systems 12A, 12B, 12C according to the first through third embodiments, in that the radiation detecting apparatus 10D comprises a flat sheet-like radiation detecting circuit unit 160, a box-like control circuit unit 162 for controlling the radiation detecting circuit unit 160. A connector 164 connected to the radiation detecting circuit unit 160 and a connector 166 connected to a cable 168 connected to the control circuit unit 162 are connected to each other, for thereby electrically connecting the radiation detecting circuit unit 160 and the control circuit unit 162 to each other.

With the radiation detecting apparatus 10A, 10B, 10C and the radiation image capturing systems 12A, 12B, 12C according to the first through third embodiments, the radiation detector 40, the cassette controller 46, etc., are housed in a single radiation detecting apparatus 10A, 10B, 10C. However, with the radiation detecting apparatus 10D and the radiation image capturing system 12D according to the fourth embodiment, the radiation detecting circuit unit 160 and the control circuit unit 162 become electrically disconnected when the connectors 164, 166 are disconnected from each other.

The radiation detecting apparatus 10D and the radiation image capturing system 12D according to the fourth embodiment differ basically from the radiation detecting apparatus 10A, 10B, 10C and the radiation image capturing systems 12A, 12B, 12C according to the first through third embodiments, as described above. Specific structural details of the radiation detecting apparatus 10D and the radiation image capturing system 12D according to the fourth embodiment will be described below.

Figure 22:
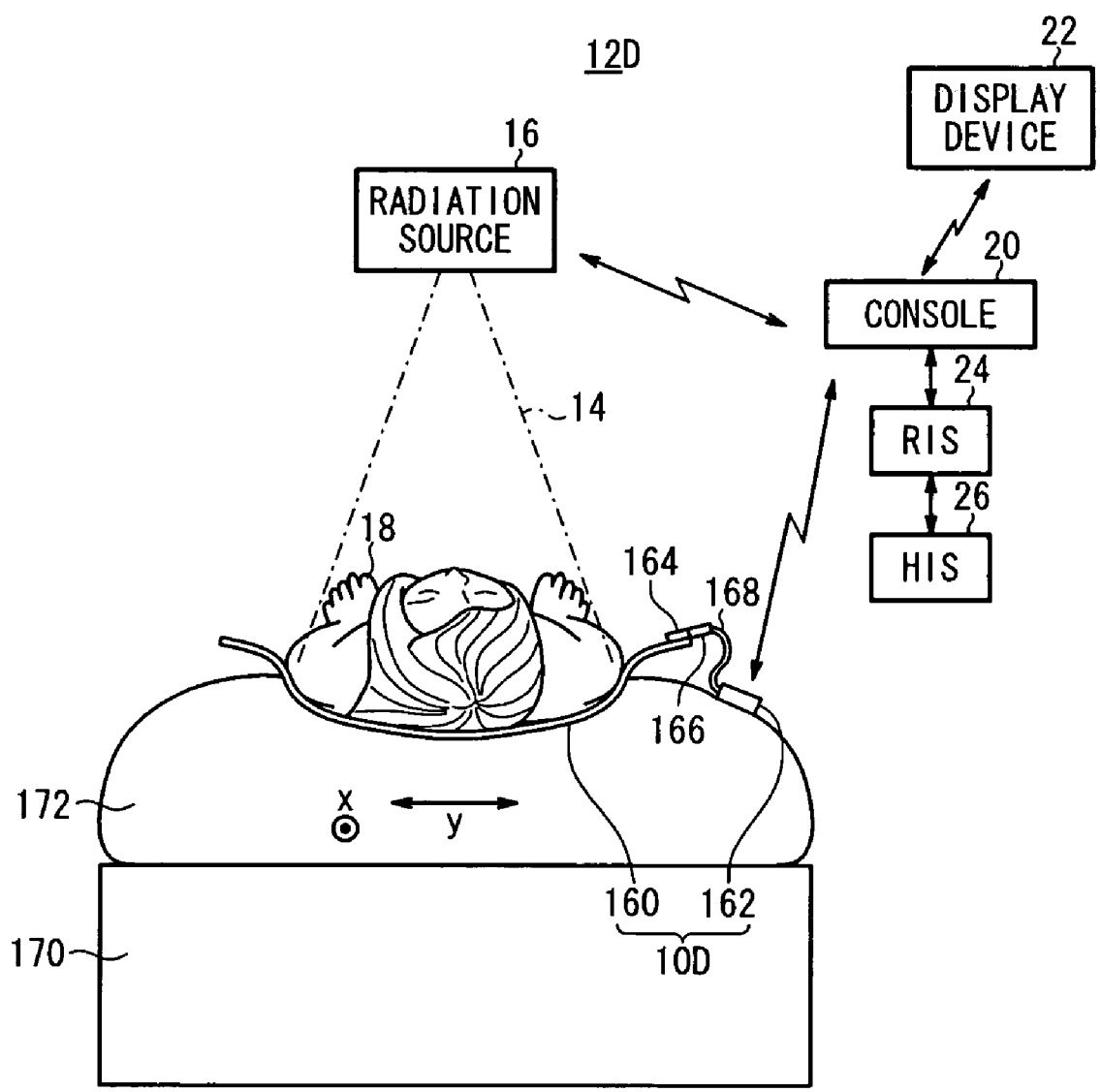
FIG. 22 is a block diagram of a radiation detecting apparatus and a radiation image capturing system according to a fourth embodiment of the present invention.

As shown in FIG. 22, the radiation image capturing system 12D according to the fourth embodiment is installed in an operating room or the like. The radiation detecting apparatus 10D, which serves as part of the radiation image capturing system 12D, comprises the flat sheet-like radiation detecting circuit unit 160, and the box-like control circuit unit 162 for controlling the radiation detecting circuit unit 160, as described above. The connector 166 is connected to one end of the cable 168, and the other end of the cable 168 is connected to the control circuit unit 162. The connector 164 is connected to an end of the radiation detecting circuit unit 160 in a longitudinal direction y thereof. The radiation detecting circuit unit 160 is flexible in the longitudinal direction y. When the connector 164 and the connector 166 are connected to each other, the radiation detecting circuit unit 160 and the control circuit unit 162 are electrically connected to each other.

The radiation detecting circuit unit 160 is interposed between a mattress 172, which is disposed on a bed 170 such as a surgical bed, and the patient (subject) 18. Since the radiation detecting circuit unit 160 is flexible in the longitudinal direction y, the radiation detecting circuit unit 160 flexes along the surface configuration of the patient 18 on the mattress 172 under the weight of the patient 18. Since the radiation detecting circuit unit 160 is pliable, it does not cause the patient 18 any pain, and lends itself to capturing a radiation image of the patient 18 on the bed 170.

Figure 23:
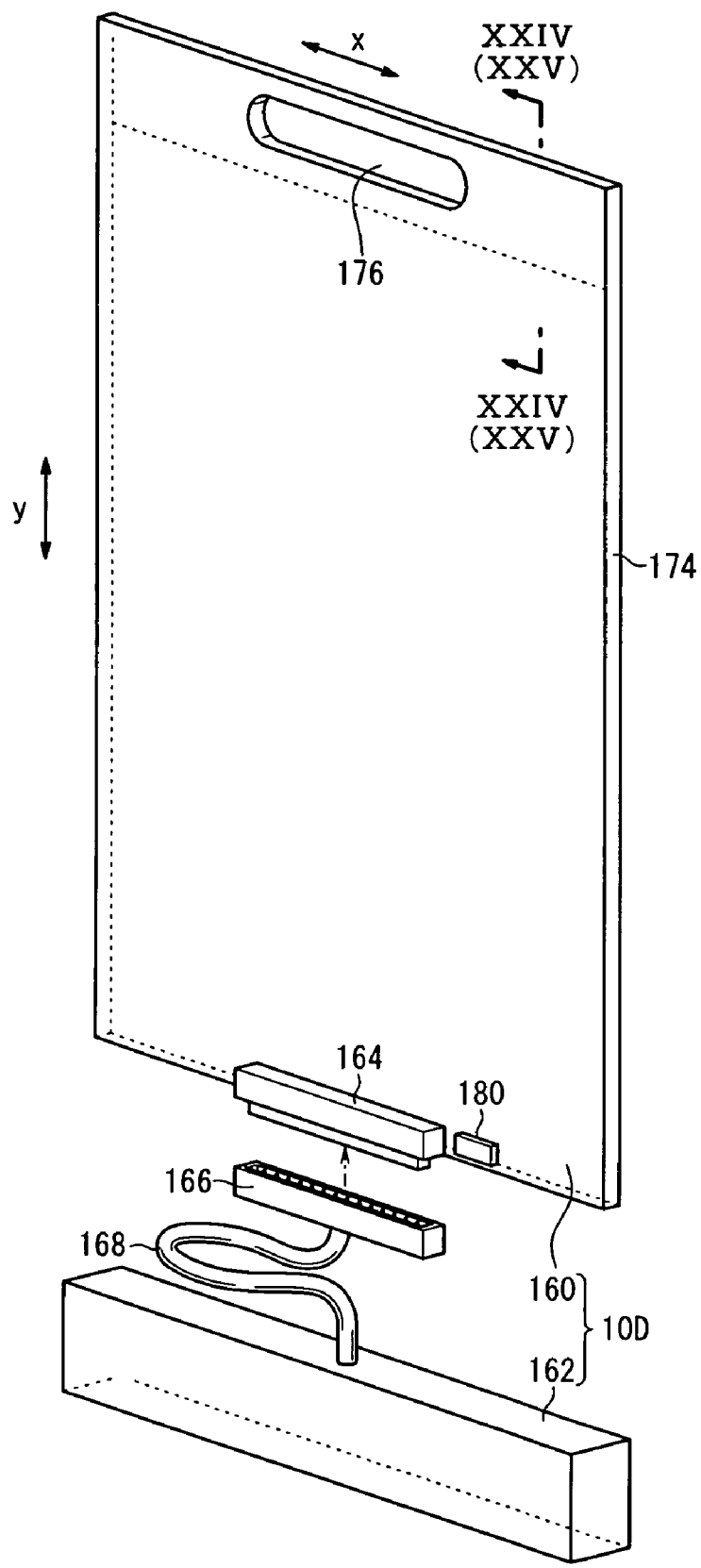
FIG. 23 is a perspective view of the radiation detecting apparatus shown in FIG. 22.

As shown in FIG. 23, the radiation detecting circuit unit 160 is disposed on a substrate 174 made of resin, which has a rectangular main surface and which is flexible (pliable) across the rectangular shape thereof. The connector 164 is mounted on an end of the substrate 174 in the longitudinal direction y and extends in a transverse direction x. Flexibility of the substrate 174 in the transverse direction x is limited by the connector 164.

The substrate 174 has an opening defined in the other end in the longitudinal direction y, providing a grip 176.

Figure 24:
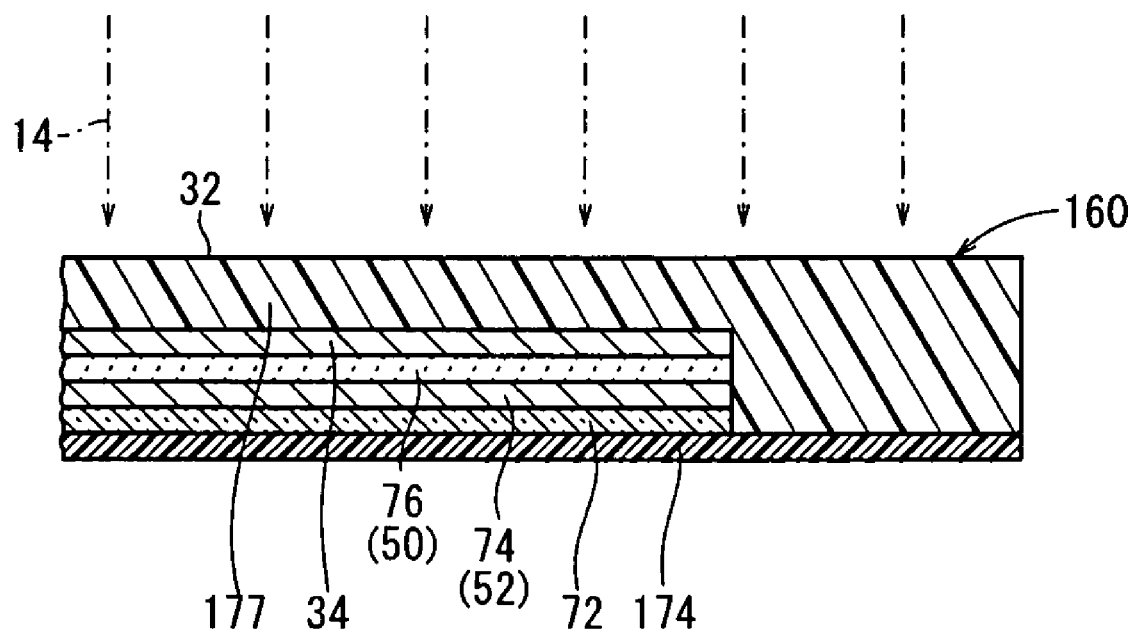
FIG. 24 is a cross-sectional view taken along line XXIV-XXIV of FIG. 23.

As shown in FIG. 24, the radiation detecting circuit unit 160 comprises a stacked assembly mounted on a surface of the substrate 174. The stacked assembly comprises a scintillator 72, a TFT layer 74, a photoelectric transducer layer 76, and a grid 34, which are successively arranged in this order from the substrate 174. The stacked assembly is covered with a protective layer 177 of resin, whose surface serves as the irradiated surface 32 to be irradiated with radiation 14. Radiation 14 that passes through the protective layer 177 is applied to the scintillator 72, which converts the radiation 14 into visible light. The visible light is converted by pixels 50 (see FIGS. 26 and 27) of the photoelectric transducer layer 76 into electric charges (electric signals), which are stored in the pixels 50. The pixels 50 are connected to a bias capacitor 180, which applies a bias voltage Vb to the pixels 50 through bias lines 178 (see FIG. 27).

The bias capacitor 180 is disposed on the substrate 174 next to the connector 164, i.e., on an end of the substrate 174 in the longitudinal direction y (see FIG. 23).

Figure 25:
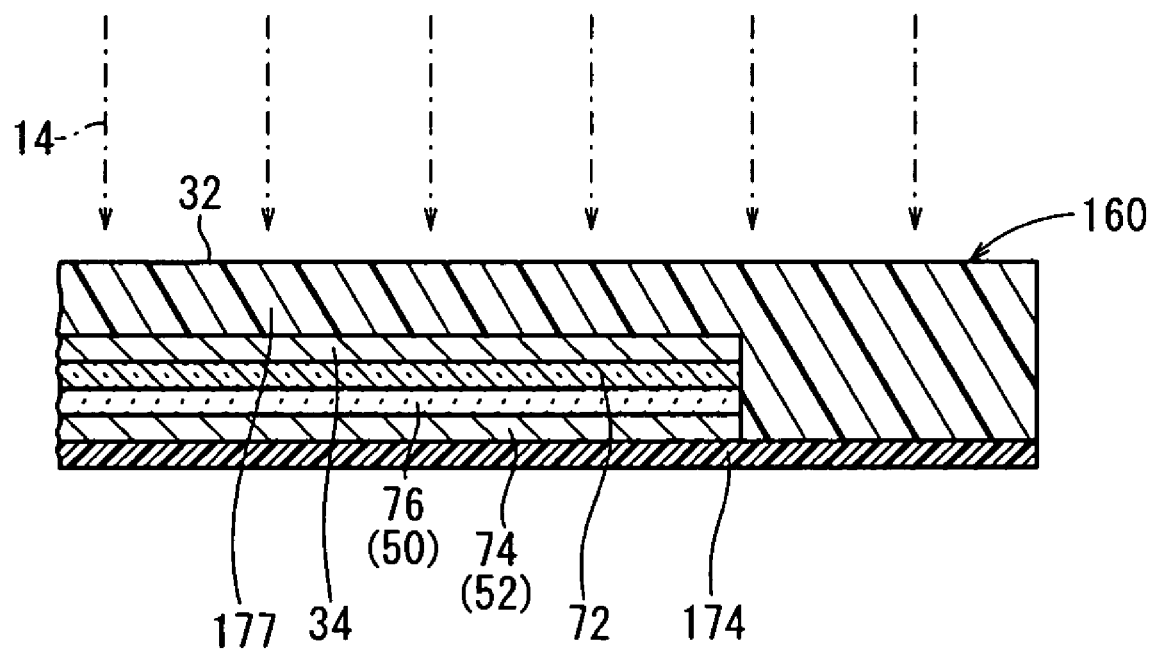
FIG. 25 is a cross-sectional view taken along line XXV-XXV of FIG. 23.

As shown in FIG. 25, the scintillator 72 is interposed between the grid 34 and the photoelectric transducer layer 76.

As is the case with the first through third embodiments, the pixels 50 may be constituted by a photoelectric transducer layer made of amorphous selenium (a-Se), rather than a-Si, having an allowable temperature range smaller than that of a-Si, and which is disposed on a matrix of TFTs 52 (TFT layer 74). According to such a modification, the scintillator 72 may be dispensed with.

The substrate 174 preferably is made of a mixture of a resin (which may be the same as the material of the substrate 71) and a powder of tungsten, for example. Since the substrate 174, which contains the powder of tungsten, covers the reverse side of the radiation detecting apparatus 10D, back scattered rays of radiation 14 are prevented from being emitted from the radiation detecting apparatus 10D. The control circuit unit 162 is covered in its entirety with a lead sheet or the like for protecting the circuit components of the control circuit unit 162 from damage by radiation 14.

Figure 26:
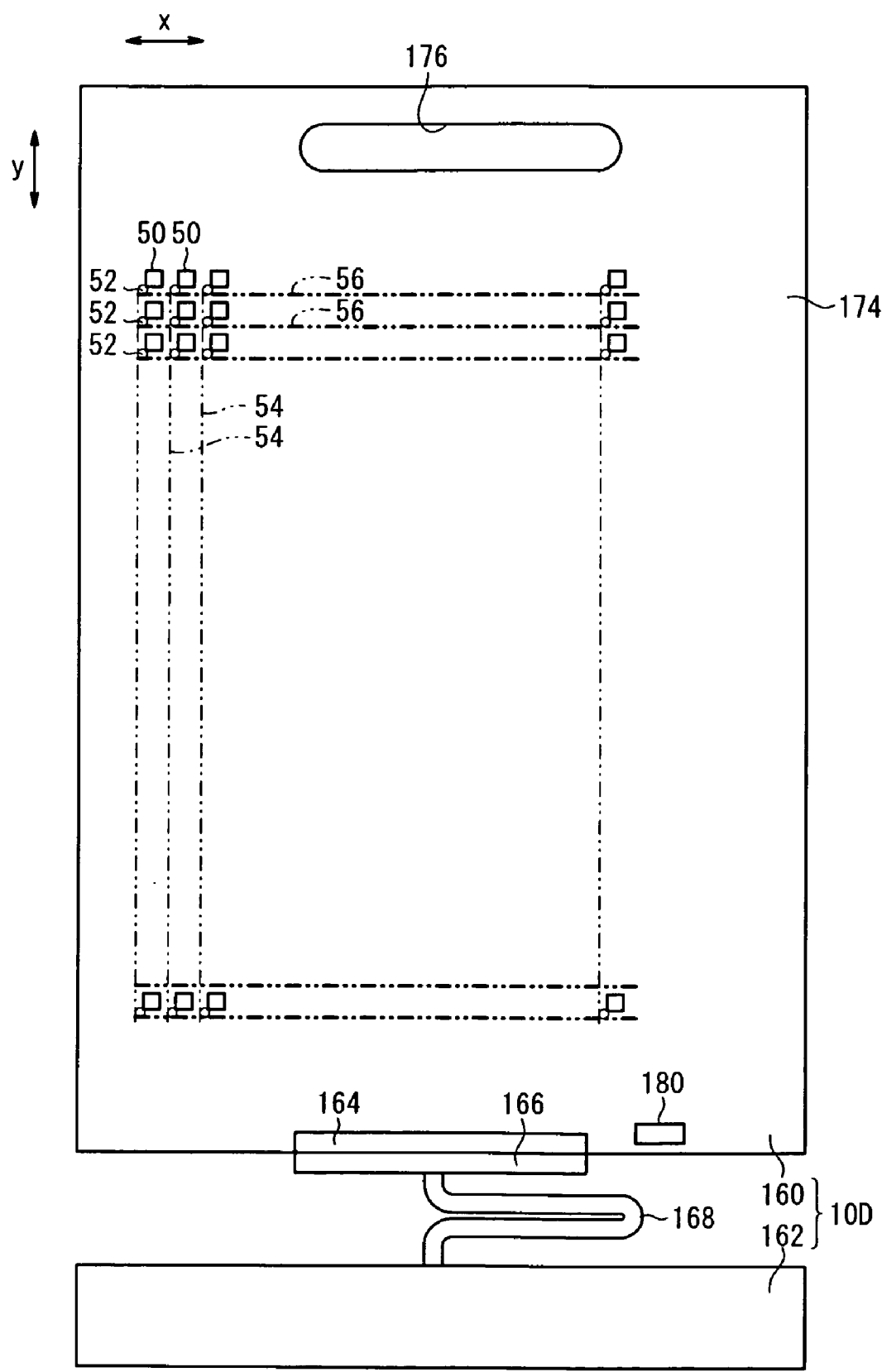
FIG. 26 is a wiring diagram of the radiation detecting apparatus shown in FIG. 23.
Figure 27:
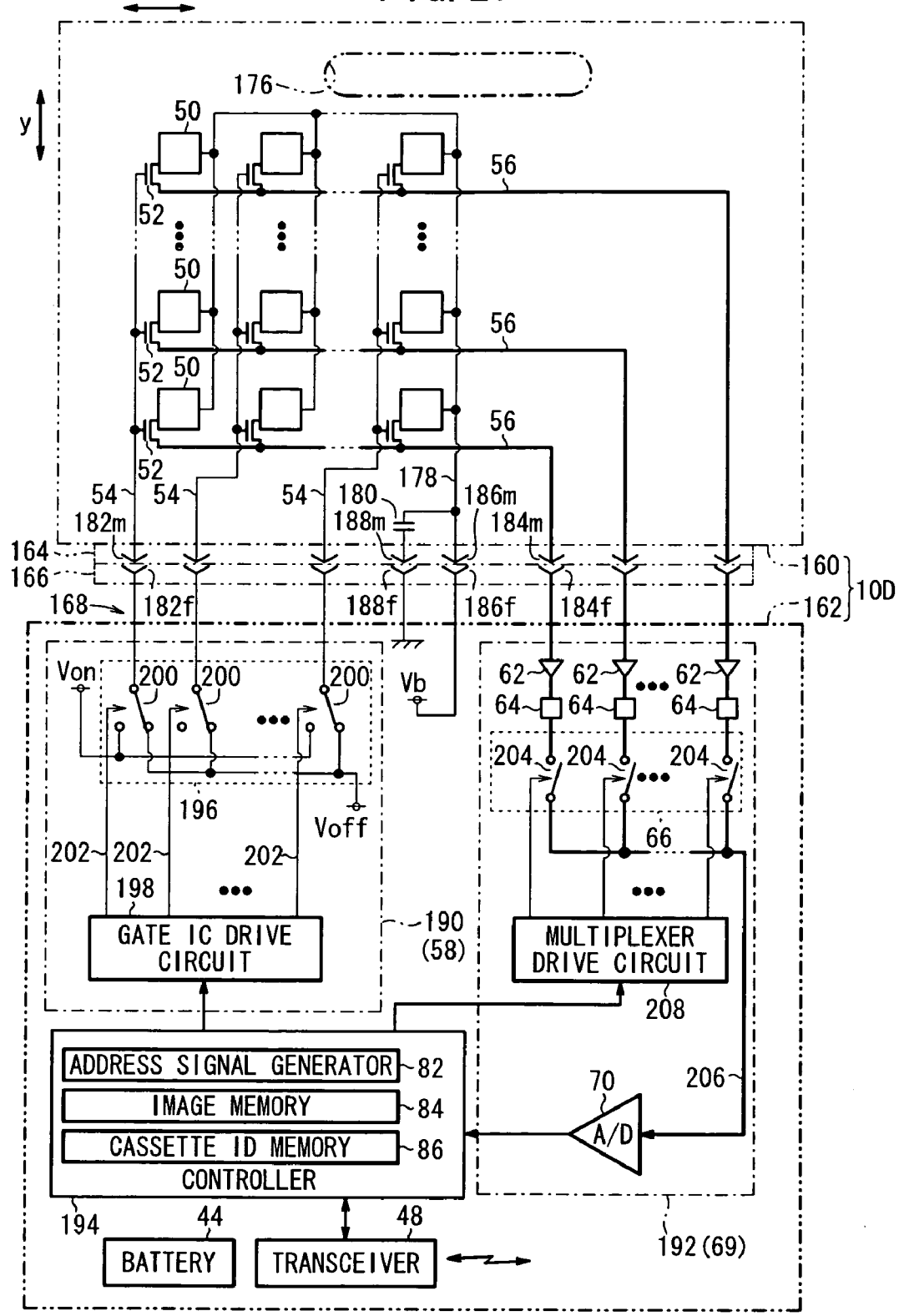
FIG. 27 is a block diagram of a circuit arrangement of the radiation detecting apparatus shown in FIG. 23.

As shown in FIGS. 26 and 27, the radiation detecting circuit unit 160 has, in a central area thereof, a matrix of pixels 50 and another matrix of TFTs 52, each having a signal electrode connected to one of the pixels 50, another signal electrode connected to a signal line 56, and a gate electrode connected to a gate line 54. In FIG. 26, each of the TFTs 52 is represented by a blank circular dot. The signal lines 56 and the gate lines 54 are connected to the pixels 50 through the TFTs 52, and the bias lines 178 (see FIG. 27) also are connected to the respective pixels 50.

The connector 164, which is connected to the radiation detecting circuit unit 160, includes input terminals 182m of the gate lines 54, output terminals 184m of the signal lines 56, a bias input terminal 186m for supplying the bias voltage Vb to the bias lines 178 connected to the bias capacitor 180, and a ground terminal 188m connected to the bias capacitor 180. The terminals 182m, 184m, 186m, 188m comprise male terminals.

The connector 166, which is connected to the control circuit unit 162, includes output terminals 182f of the gate lines 54, input terminals 184f of the signal lines 56, a bias output terminal 186f for supplying the bias voltage Vb to the bias lines 178 connected to the bias capacitor 180, and a ground terminal 188f connected to ground. The terminals 182f, 184f, 186f, 188f comprise female terminals.

The control circuit unit 162 comprises a gate drive circuit 190 functioning as the line scanning driver 58 for energizing the columns of the TFTs 52 through the gate lines 54, a signal reading circuit 192 functioning as the reading circuit 69 for reading signal charges (electric charges) supplied through the energized TFTs 52 and the signal lines 56, a bias power supply for applying the bias voltage Vb to the pixels 50 through the bias lines 178, the battery (battery unit) 44 serving as a power supply for the radiation detecting apparatus 10D, a controller 194, which functions the same as the cassette controller 46 of the radiation detecting apparatus 10A through 10C for controlling the radiation detecting apparatus 10D in its entirety, and a transceiver 48 for sending, to the console 20, signals including information of the radiation 14 (radiation image information), which is detected by the radiation detecting circuit unit 160, read by the signal reading circuit 192, and stored in the image memory 84.

The gate drive circuit 190 comprises a gate IC 196 and a gate IC drive circuit 198 for energizing the gate IC 196, which has the same functions as the address decoder 60 (see FIG. 5).

The gate IC 196 includes an array of one-circuit two-contact electronic switches 200, which are similar in structure to the switches SW1 of the line scanning driver 58. The electronic switches 200 have movable contacts connected to the respective gate lines 54, and fixed contacts supplied with the control signals Von, Voff (hereinafter referred to as a gate-on voltage Von and a gate-off voltage Voff).

When radiation 14 is applied to the radiation detecting circuit unit 160, while the electronic switches 200 are supplied with the gate-off voltage Voff under the control of control signals supplied from the gate IC drive circuit 198 through respective control lines 202, the pixels 50 store signal charges.

When the electronic switches 200 are subsequently supplied with the gate-on voltage Von under the control of control signals supplied from the gate IC drive circuit 198 through the respective control lines 202, the TFTs 52 connected to the gate lines 54 and arrayed along the columns (i.e., in the longitudinal direction y) are turned on, thereby allowing the signal charges stored in the pixels 50 to flow into the signal lines 56.

The signal reading circuit 192 comprises an array of amplifiers 62 (also referred to as integral amplifiers 62) in the form of ICs (integrated circuits) connected respectively to the signal lines 56, an array of sample and hold circuits 64 connected to the respective amplifiers 62, an array of electronic switches 204, which are similar in structure to the switches SW2 (see FIG. 5) of the multiplexer 66 and are connected to the respective sample and hold circuits 64, and an A/D converter 70 having an input terminal connected to the movable contacts of the electronic switches 204 through a signal line 206, and an output terminal connected to the controller 194.

The signal reading circuit 192 also includes a multiplexer drive circuit 208, which has the same functions as the address decoder 68, for energizing or turning on the electronic switches 204 successively for the signal lines 56, i.e., successively for the rows arrayed in the transverse direction x. An analog signal voltage, which is represented by signal charges supplied from the signal lines 56, is converted into a digital signal voltage by the A/D converter 70.

The controller 194 comprises an address signal generator 82 (also referred to as an address signal generating circuit 82) for supplying an address signal to the gate IC drive circuit 198 and the multiplexer drive circuit 208, an image memory 84, and a cassette ID memory 86 (also referred to as an ID memory 86).

As described above, the pixels 50 store signal charges generated when the visible light converted from the radiation 14 is further converted into electric signals. When the TFTs 52 are turned on by the electronic switches 200 successively for the columns in the transverse direction x, and are turned on by the electronic switches 204 successively for the rows in the longitudinal direction y, the signal charges stored in the pixels 50 are read as digital image signals representing the radiation image information that is borne by the radiation 14.

The radiation detecting apparatus 10D and the radiation image capturing system 12D according to the fourth embodiment are constructed as described above. Operations of the radiation detecting apparatus 10D and the radiation image capturing system 12D according to the fourth embodiment will be described below.

The radiation image capturing system 12D according to the fourth embodiment is installed in an operating room or the like, and is used when radiation image information of the patient 18 needs to be captured while a surgical operation is being performed on the patient 18 by a doctor, for example. As with the first through third embodiments, patient information of the patient 18 to be imaged along with image capturing conditions for the patient 18 are registered in the console 20 prior to performing the image capturing process. After such a preparatory process is finished, the surgical operation is performed on the patient 18.

For capturing radiation image information of the patient 18 during the surgical operation, the doctor or a radiological technician positions the radiation detecting circuit unit 160 (see FIGS. 24 and 25) in a given position between the patient 18 and the mattress 172 on the bed 170, with the irradiated surface 32 of the radiation detecting circuit unit 160 facing the radiation source 16. Thereafter, the doctor or radiological technician connects the connector 166 to the connector 164 of the radiation detecting circuit unit 160, so as to connect the control circuit unit 162 to the radiation detecting circuit unit 160. In this manner, the doctor or radiological technician places the radiation detecting apparatus 10D on the mattress 172.

After having moved the radiation source 16 to a position facing the radiation detecting circuit unit 160, the doctor or radiological technician operates an image capturing switch, not shown, of the radiation source 16. The radiation source 16 acquires image capturing conditions for a region to be imaged of the patient 18 from the console 20 by way of wireless communications, controls a dose regulator in the radiation source 16 according to the acquired image capturing conditions, and applies radiation 14 at a controlled dose to the patient 18.

Radiation 14 passes through the patient 18 and then is applied to the radiation detecting circuit unit 160. The radiation 14 is applied to the grid 34 of the radiation detecting circuit unit 160, which removes scattered rays from the radiation 14. Then, the pixels 50 of the radiation detecting circuit unit 160 convert the radiation 14 into electric signals, which are stored as electric charges (signal charges). The stored signal charges, which represent radiation image information of the patient 18, are read from the pixels 50 according to address signals, which are supplied from the address signal generator 82 of the controller 194 to the gate IC drive circuit 198 and the multiplexer drive circuit 208.

Specifically, the gate IC drive circuit 198 outputs a selection signal according to an address signal supplied from the address signal generator 82, so as to turn on an electronic switch 200 corresponding to the selection signal and thereby select a gate line 54, and applies the gate-on voltage Von to the gate electrodes of the TFTs 52 arrayed in the column connected to the selected gate line 54. The gate IC drive circuit 198 applies the gate-off voltage Voff to gate lines 54 which are not selected. The multiplexer drive circuit 208 outputs selection signals according to the address signals supplied from the address signal generator 82, so as to successively switch between the electronic switches 204 of the multiplexer 66, and successively reads, through the signal lines 56, signal charges representing the radiation image information from the pixels 50 connected to the gate line 54 and selected by the gate IC drive circuit 198.

The signal charges read from the pixels 50 are amplified by the integral amplifiers 62, sampled by the sample and hold circuits 64, and supplied through the multiplexer 66 (electronic switches 204) and the signal line 206 to the A/D converter 70, which converts the signal charges into digital image signals. The digital image signals, which represent the radiation image information, are temporarily stored in the image memory 84 of the controller 194.

The gate IC drive circuit 198 successively switches between columns of the TFTs 52 connected to the gate lines 54, according to address signals supplied from the address signal generator 82. The multiplexer drive circuit 208 reads the signal charges representing the radiation image information from the pixels 50 through the signal lines 56, through the integral amplifiers 62, the sample and hold circuits 64, the multiplexer 66, and the signal line 206 to the A/D converter 70, which converts the signal charges into digital image signals. The digital image signals are temporarily stored in the image memory 84 of the controller 194.

The radiation image information, which is represented by digital image signals stored in the image memory 84, is transmitted from the transceiver 48 to the console 20 by way of wireless communications. The console 20 processes the received radiation image information, and sends the processed radiation image information to the display device 22, which in turn displays a radiation image of the patient 18 based on the radiation image information. Therefore, the doctor can continue the surgical operation on the patient 18, while simultaneously confirming the radiation image displayed on the display device 22.

As described above, with the radiation detecting apparatus 10D and the radiation image capturing system 12D according to the fourth embodiment, the radiation detecting apparatus 10D on the flexible substrate 174 includes the matrix of TFTs 52 (TFT layer 74) having signal electrodes connected to the signal lines 56, gate electrodes connected to the gate lines 54, and other signal electrodes connected to the pixels 50 (photoelectric transducer layer 76) for detecting radiation 14 that has passed through the patient 18 and converting the radiation 14 into signal charges, the pixels 50 disposed respectively on the TFTs 52, the bias capacitor 180 for applying the bias voltage Vb to the pixels 50, the input terminals 182*m* of the gate lines 54, the output terminals 184*m* of the signal lines 56, and the bias input terminal 186*m* for supplying the bias voltage Vb to the bias capacitor 180.

Since the matrix of TFTs 52 with the pixels 50 disposed thereon, the bias capacitor 180 for biasing the pixels 50, and the connector 164 including the input terminals 182*m*, etc., are all disposed on the flexible substrate 174 of the radiation detecting apparatus 10D, the radiation detecting apparatus 10D (radiation detecting circuit unit 160) is flexible, flat and lightweight.

As described above, the radiation detecting apparatus 10D comprises the radiation detecting circuit unit 160 disposed on the flexible substrate 174, and the control circuit unit 162 for controlling the radiation detecting circuit unit 160.

The radiation detecting circuit unit 160 includes the matrix of TFTs 52, the bias capacitor 180, the input terminals 182*m*, the output terminals 184*m*, and the bias input terminal 186*m* (connector 164). The control circuit unit 162 includes the gate drive circuit 190 for energizing the columns of TFTs 52, and the signal reading circuit 192 for reading signal charges from the rows of pixels 50 through the energized columns of TFTs 52.

As described above, since the radiation detecting circuit unit 160 of the radiation detecting apparatus 10D includes the matrix of TFTs 52 with the pixels 50 disposed thereon, the bias capacitor 180 for biasing the pixels 50, and the connector 164 for energizing the TFTs 52 and reading signal charges from the pixels 50 (the input terminals 182*m* for energizing the TFTs 52, the output terminals 184*m* for reading signal charges from the pixels 50, the bias input terminal 186*m* for supplying the bias voltage Vb to the pixels 50, and the ground terminal 188*m* for grounding the radiation detecting circuit unit 160), all of which are disposed on the flexible substrate 174, the radiation detecting circuit unit 160 is made flexible in configuration.

In other words, since the radiation detecting circuit unit 160 does not include the control circuit unit 162 therein, the radiation detecting circuit unit 160 is made both flat and lightweight. Since the radiation detecting circuit unit 160 can flex in accordance with the surface configuration of the patient 18, the radiation detecting circuit unit 160 is less burdensome on the patient 18.

When the pixels 50 store signal charges, the TFTs 52 may be turned off and the bias voltage Vb may be applied to the pixels 50. Therefore, even when the connector 164 connected to the radiation detecting circuit unit 160 and the connector connected to the control circuit unit 162 are not interconnected, the radiation image information (signal charges) can still be captured by the radiation detecting circuit unit 160 (pixels 50), provided the bias voltage Vb is applied to the bias capacitor 180.

Specifically, when the connectors 164, 166 are not connected to each other, the radiation detecting circuit unit 160

(pixels 50) can store the radiation image information (signal charges), which represents the radiation 14 that has passed through the patient 18, by applying the bias voltage Vb to (the input terminal 186*m* of) the bias capacitor 180 through a clip, for example, which serves to apply the bias voltage Vb more reliably. After the radiation detecting circuit unit 160 (pixels 50) has stored the radiation image information (signal charges) therein, the clip is removed, the connectors 164, 166 are disconnected from each other, and the TFTs 52 are energized by the gate drive circuit 190 in order to cause the signal reading circuit 192 to read the radiation image information (signal charges) from the pixels 50, and store the read radiation image information in the image memory 84 of the controller 194.

Figure 28:
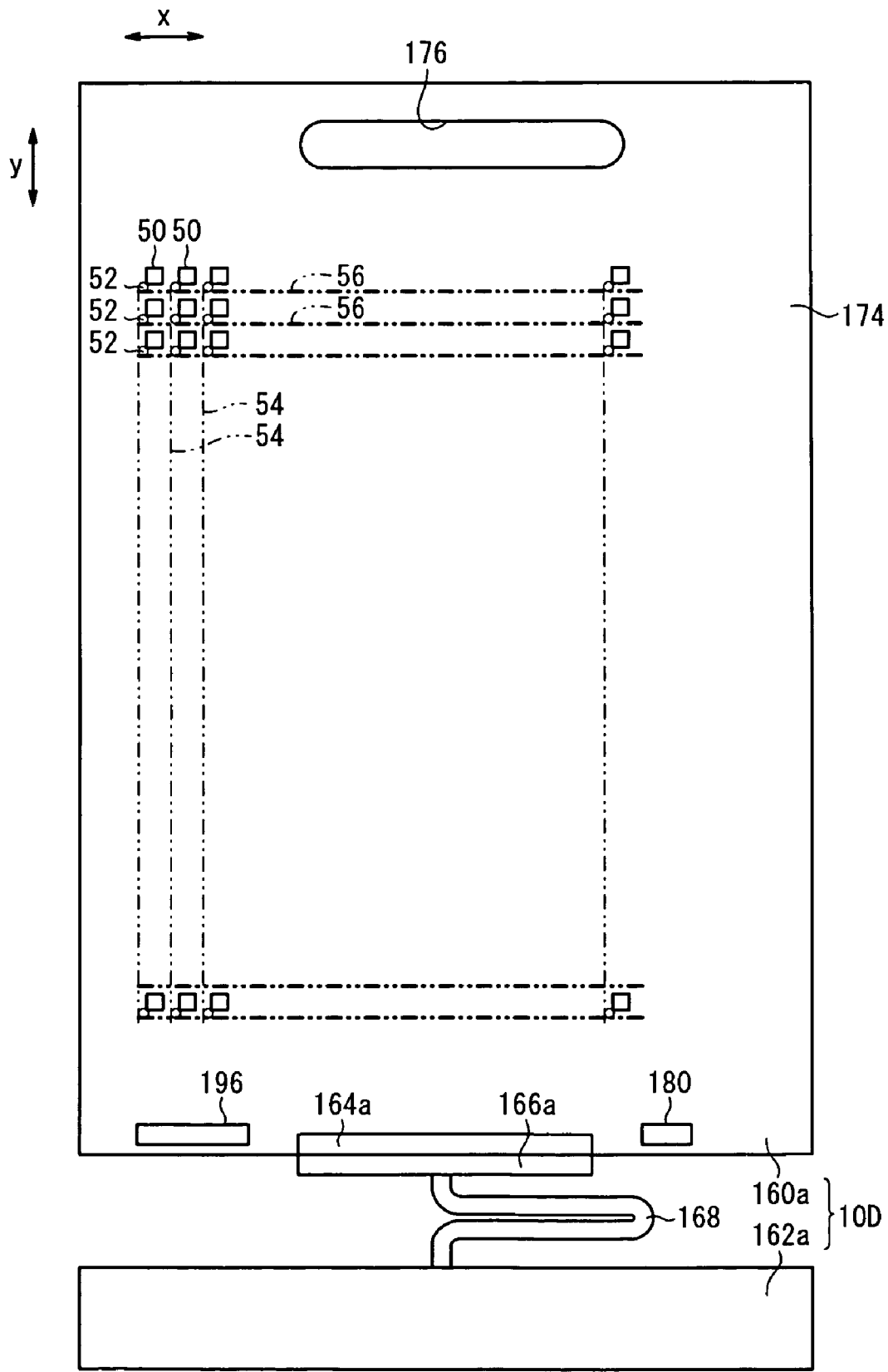
FIG. 28 is a wiring diagram of another arrangement of the radiation detecting apparatus according to the fourth embodiment.
Figure 29:
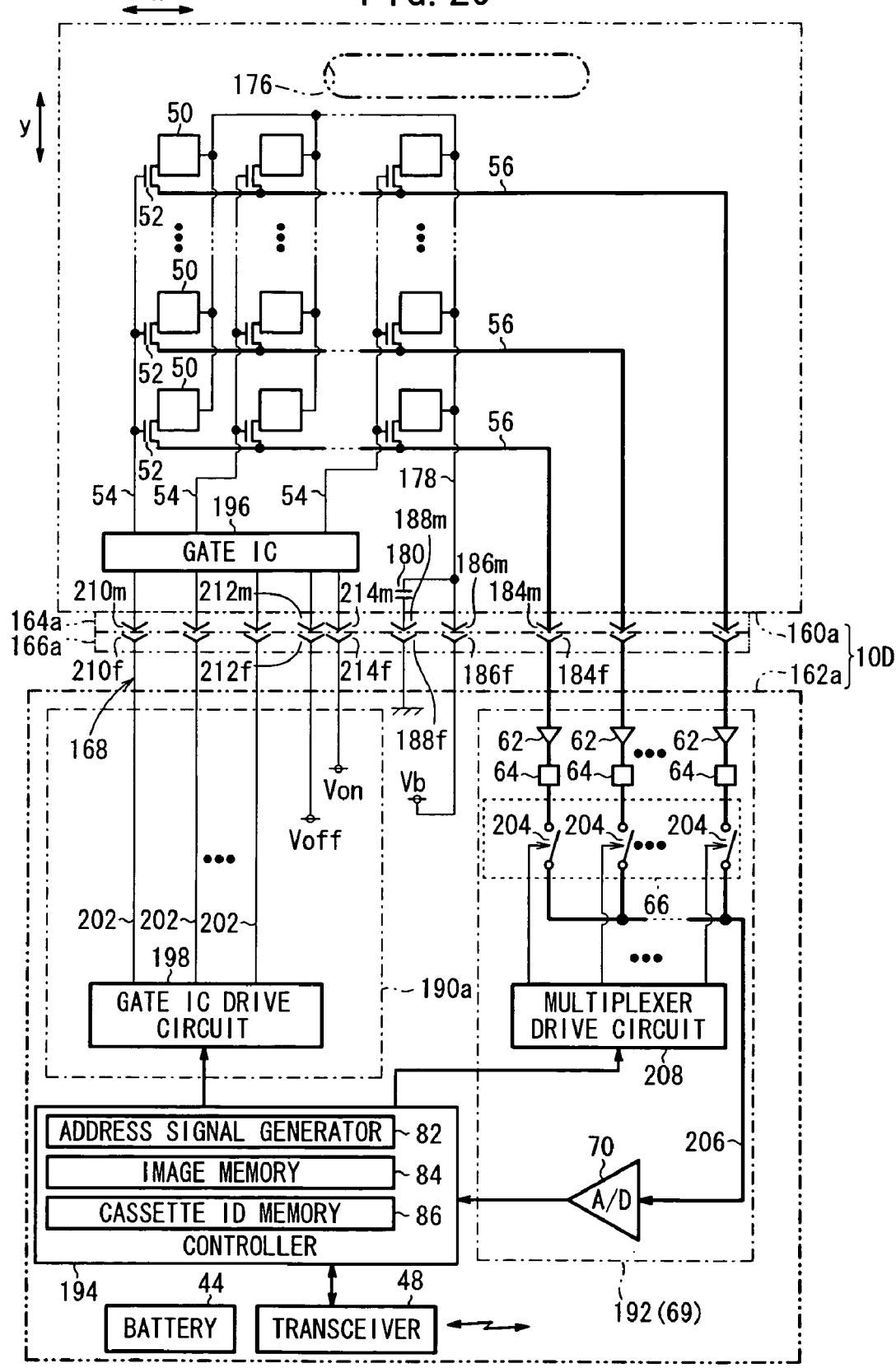
FIG. 29 is a block diagram of a circuit arrangement of the radiation detecting apparatus shown in FIG. 28.

The radiation detecting apparatus 10D according to the fourth embodiment may have an arrangement (first modification) as shown in FIGS. 28 and 29.

According to such a first modification, the gate IC 196 is mounted on a radiation detecting circuit unit 160*a*. The gate IC 196, which is mounted on the radiation detecting circuit unit 160*a*, is spaced from the TFTs by a short physical distance, thereby reducing stray impedance (including an inductance and a capacitance) and energizing the TFTs 52 at a high speed. As a result, the signal charges stored in the pixels 50 can be read at a high speed.

According to the first modification, furthermore, the control lines 202 in a control circuit unit 162*a* and the lines for supplying the gate-on voltage Von and the gate-off voltage Voff are connected to each other by output terminals 210*f* and input terminals (drive terminals) 210*m*, an output terminal 212*f* and an input terminal (drive terminal) 212*m*, and an output terminal 214*f* and an input terminal (drive terminal) 214*m* of connectors 166*a*, 166*b*. The control circuit unit 162*a* includes a gate drive circuit 190*a* comprised of only the gate IC drive circuit 198.

Figure 30:
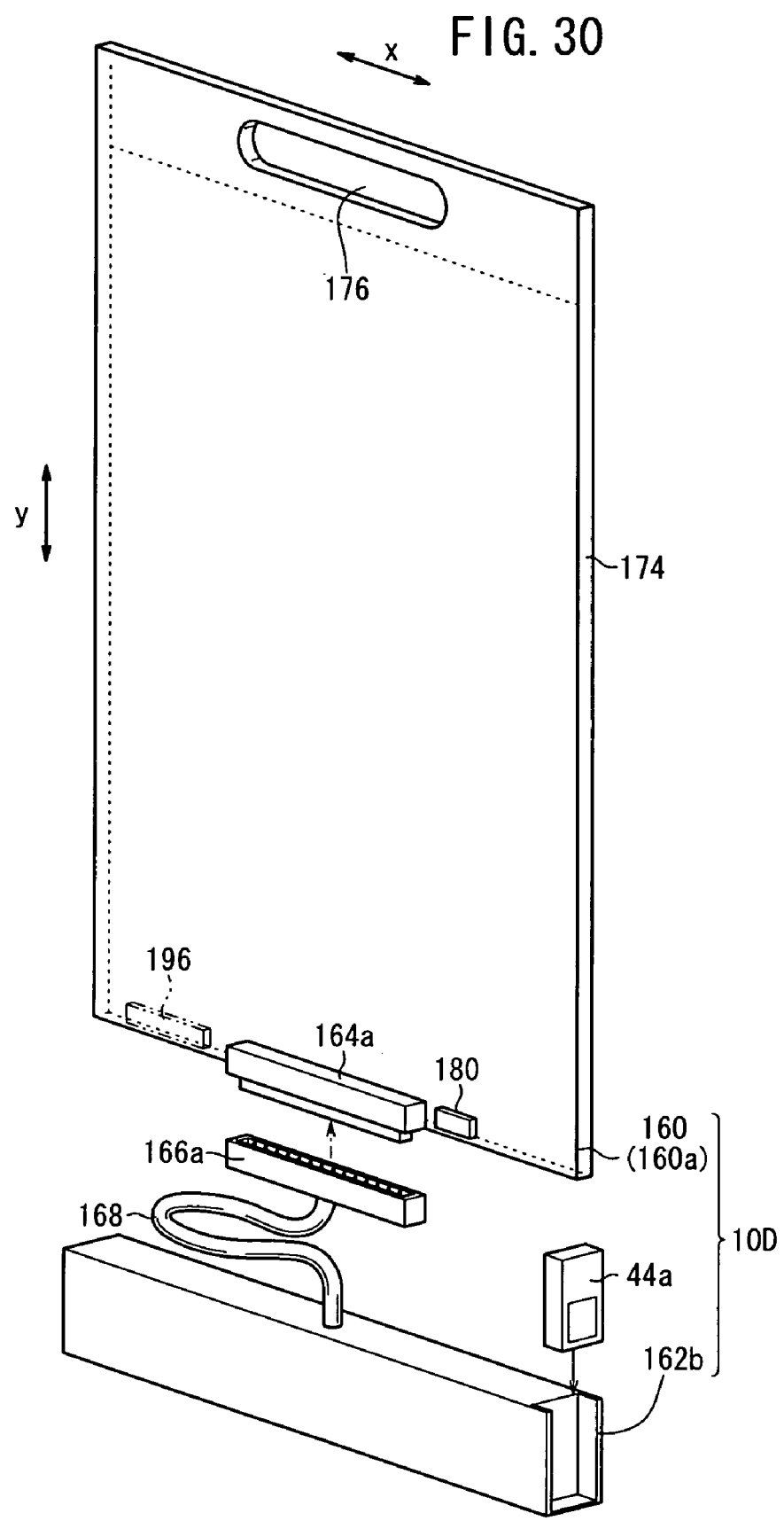
FIG. 30 is a perspective view of still another modification of the radiation detecting apparatus according to the fourth embodiment.

The radiation detecting apparatus 10D according to the fourth embodiment may also incorporate the arrangement (second modification) shown in FIG. 30.

According to the second modification, a battery pack 44*a* (battery unit) that includes the battery 44 is detachably mounted on a control circuit unit 162*b*, which does not incorporate the battery 44 per se. Since the battery 44 is separate and replaceable, an amount of radiation image information, i.e., a given number of radiation images of the patient 18 or a plurality of patients 18, may be obtained using a plurality of replaceable battery packs 44*a*.

The second modification is applicable to the arrangement shown in FIGS. 26 and 27 and the arrangement (first modification) shown in FIGS. 28 and 29.

Specifically, if the second modification is applied to the arrangement shown in FIGS. 26 and 27, then the radiation detecting apparatus 10D is made up of the radiation detecting circuit unit 160, on which the gate IC 196 is not mounted, the control circuit unit 162*b* (see FIG. 30), on which the battery 44 is not mounted, and the battery pack 44*a*.

If the second modification is applied to the arrangement shown in FIGS. 28 and 29, then the radiation detecting apparatus 10D is made up of the radiation detecting circuit unit 160, on which the gate IC 196 is mounted, the control circuit unit 162*b* (see FIG. 30), on which the battery 44 is not mounted, and the battery pack 44*a*.

The present invention is not limited to the above embodiments and modifications thereof, but various changes and other modifications may be made within the scope of the invention.

For example, according to the fourth embodiment, while a surgical operation is performed on the patient 18, the radiation image capturing system 12D is used to display a radiation image of the patient 18 on the display device 22. However, the radiation image capturing system 12D may be used to capture radiation image information of the patient 18 when a surgical operation is not being performed on the patient 18. For example, the radiation image capturing system 12D may be used while the doctor examines the patient 18, or when the doctor goes on rounds in the hospital.

When the radiation detecting apparatus 10D is used in an operating room or the like, blood stains and other contaminants may be applied to the radiation detecting apparatus 10D. The radiation detecting apparatus 10D may have a water-resistant sealed structure, so that the radiation detecting apparatus 10D can be sterilized and cleaned to remove such blood stains and contaminants, thereby enabling the radiation detecting apparatus 10D to be used repeatedly.

Although certain preferred embodiments of the present invention have been shown and described in detail, it should be understood that various changes and modifications may be made to the embodiments without departing from the scope of the invention as set forth in the appended claims.

What is claimed is:

1. A radiation detecting apparatus comprising:
    a radiation conversion panel for detecting radiation that has passed through a subject and converting the detected radiation into radiation image information; and
    a casing for storing the radiation conversion panel which is wound into a roll and stored when the subject is not irradiated with the radiation,
    wherein when the subject is irradiated with the radiation, the radiation conversion panel stored as a roll in the casing is unrolled and pulled out of the casing, and the radiation conversion panel is extended flatwise against the subject.

2. A radiation detecting apparatus according to claim 1, further comprising:
    a screen which can be rolled and stored in the casing, the radiation conversion panel being incorporated in the screen;
    a takeup shaft disposed in the casing for rolling the screen therearound; and
    a weight bar disposed outside of the casing,
    wherein the screen has a proximal end connected to the takeup shaft and a distal end connected to the weight bar.

3. A radiation detecting apparatus according to claim 2, wherein the weight bar houses therein at least one of a battery for energizing the radiation conversion panel, a controller for controlling the radiation conversion panel, a wireless communicating unit for performing wireless communication with an external circuit, and an interface unit for sending information to and receiving information from an external device.

4. A radiation detecting apparatus according to claim 2, wherein the weight bar has a handle for pulling the screen, which is rolled around the takeup shaft inside the casing, out of the casing.

5. A radiation detecting apparatus according to claim 2, having a suspended structure or an upstanding structure, wherein the subject is irradiated with the radiation while the screen is extended vertically flatwise against the subject while the subject is held in an upright posture.

6. A radiation detecting apparatus according to claim 2, wherein the screen has an irradiated surface, which is irradiated with the radiation through the subject, the irradiated surface having a marker serving as a reference mark for an image capturing area and an image capturing position with respect to the subject.

7. A radiation detecting apparatus according to claim 2, the radiation detecting apparatus comprising a radiation detecting cassette, wherein the screen is made of a material permeable to the radiation.

8. A radiation detecting apparatus according to claim 1, wherein the radiation conversion panel comprises a scintillator for converting the radiation into visible light, a plurality of solid-state detectors for converting the visible light into electric signals, and a reader for reading the electric signals from the solid-state detectors and acquiring the read electric signals as the radiation image information.

9. A radiation detecting apparatus according to claim 8, wherein the solid-state detectors and the scintillator are successively arranged in order toward the subject, or the scintillator and the solid-state detectors are successively arranged in order toward the subject.

10. A radiation detecting apparatus according to claim 1, wherein the casing includes at least one of a display unit for displaying information concerning the radiation detecting apparatus, and a handle for carrying the casing with the radiation conversion panel housed therein.

11. A radiation detecting apparatus according to claim 1, wherein by pulling the radiation conversion panel as a roll out of the casing, the radiation conversion panel is ready for image capturing.

12. A radiation image capturing system comprising:
a radiation source for emitting radiation;
a radiation detecting apparatus comprising a radiation conversion panel for detecting radiation that has been emitted from the radiation source and passed through a subject and converting the detected radiation into radiation image information, and a casing for storing the radiation conversion panel which is wound into a roll and stored when the subject is not irradiated with the radiation, wherein when the subject is irradiated with the radiation, the radiation conversion panel stored as a roll in the casing is unrolled and pulled out of the casing, and the radiation conversion panel is extended flatwise against the subject; and
a controller for controlling the radiation source and the radiation detecting apparatus.

13. A radiation image capturing system according to claim 12, wherein the radiation detecting apparatus sends the radiation image information converted by the radiation conversion panel to the controller by way of wireless communications.

14. A radiation image capturing system comprising:
a radiation source for emitting radiation;
a radiation detecting apparatus for detecting the radiation that has been emitted from the radiation source and passed through a subject and converting the detected radiation into radiation image information; and
a controller for controlling the radiation source and the radiation detecting apparatus;
wherein the radiation detecting apparatus comprises:
a radiation detecting circuit unit disposed on a flexible substrate; and
a control circuit unit for controlling the radiation detecting circuit unit;
wherein the radiation detecting circuit unit comprises:
a matrix of switching devices having signal electrodes connected to signal lines, gate electrodes connected to gate lines, and other signal electrodes connected to pixels for detecting a radiation that has passed through a subject and converting the detected radiation into signal charges, the pixels being disposed respectively on the switching devices;
a gate IC for energizing columns of the switching devices;
a bias capacitor for applying a bias voltage to the pixels; and
input terminals of the gate lines, output terminals of the signal lines, and a bias input terminal for supplying the bias voltage to the bias capacitor; and
wherein the control circuit unit comprises:
a gate IC drive circuit for energizing the gate IC; and
a signal reading circuit for reading signal charges from rows of the pixels through energized columns of the switching devices.

15. A radiation detecting apparatus comprising:
a radiation conversion panel for detecting radiation that has passed through a subject and converting the detected radiation into radiation image information; and
a casing for storing the radiation conversion panel as a roll when the subject is not irradiated with the radiation,
wherein when the subject is irradiated with the radiation, the radiation conversion panel stored as a roll in the casing is unrolled and pulled out of the casing, and the radiation conversion panel is extended flatwise against the subject;
the radiation detecting apparatus further comprising:
a screen which can be rolled and stored in the casing, the radiation conversion panel being incorporated in the screen;
a takeup shaft disposed in the casing for rolling the screen therearound; and
a weight bar disposed outside of the casing,
wherein the screen has a proximal end connected to the takeup shaft and a distal end connected to the weight bar.

* * * * *